United States Patent [19]
Bonnefoy et al.

[11] Patent Number: 6,143,871
[45] Date of Patent: Nov. 7, 2000

[54] IL-13 AND IL-4 BINDING POLYPEPTIDES

[76] Inventors: Jean-Yves Bonnefoy, Centre d'Immunologie, Pierre Fabre, 74164 Sant Julien-en-Genevois Cedex, France; Jean-François Gauchat, Glaxo Wellcome Research and Development SA, 14 chemin des Aulx, 1228 Plan-les-Ouatres, Geneva, Switzerland

[21] Appl. No.: 08/969,125

[22] Filed: Nov. 12, 1997

[30] Foreign Application Priority Data

Dec. 13, 1996 [GB] United Kingdom .................. 9625899

[51] Int. Cl.$^7$ .......................... C07K 14/00; A61K 38/02; A61K 38/17; C07H 21/04
[52] U.S. Cl. .......................... 530/351; 530/350; 530/300; 536/23.5; 536/23.1; 435/7.1; 435/69.1; 314/2
[58] Field of Search .................................. 530/350, 351, 530/300; 536/23.5, 23.1; 514/2; 930/140–145; 435/7.1, 69.1, 172.1

[56] References Cited

FOREIGN PATENT DOCUMENTS

WO 97/20926  6/1997  WIPO .
WO 97/31946  9/1997  WIPO .

OTHER PUBLICATIONS

George et al., Current Methods in Sequence Comparison and Analysis, selected methods and applications. Edited by David H. Schlesinger, Alan R. Liss, Inc., New York, pp. 124–129, 1988.

Ngo, J. T. et al Computational complexity, protein structure prediction, and the levinthal paradox., The Protein folding problem and Tertiary structure prediction, K. Merz, Jr. And S. Le Grand, editors, Birkhause Boston., pp. 491–495, 1995.

Bowie et al., Deciphering the message in Protein sequences: Tolerance to Amino Acid Substitutions. Science, vol. 247, pp. 1306–1310, 1990.

Wells, J. A et al., Additivity of mutational effects in proteins, Biochemistry, pp. 8509–8579, 1990.

Caput et al, "Cloning and Characterization of a Specific Interleukin (IL)–13 Binding Protein Structurally Related to the IL–5 Receptor α Chain", The Journal of Biological Chemistry 271(28):16921–16926 (1996).

Minty et al, "Interleukin–13 is a new human lymphokine regulating inflammatory and immune responses", Nature 362:248–250 (1993).

Aman et al, "cDNA Cloning and Characterization of the Human Interleukin 13 Receptor α Chain", The Journal of Biological Chemistry, 271(46):29265–29270 (1996).

Hilton et al, "Cloning and characterization of a binding subunit of the interleukin 13 receptor that is also a component of the interleukin 4 receptor", Proc. Natl. Acad. Sci. USA 93:497–501 (1996).

Callard et al, "IL–4 and IL–13 receptors: are they one and the same?", Immunology Today 17(3):108–110 (1996).

*Primary Examiner*—Elizabeth Kemmerer
*Assistant Examiner*—Nirmaz S. Basi
*Attorney, Agent, or Firm*—Nixon & Vanderhye P.C.

[57] ABSTRACT

Polypeptides capable of binding human IL-13 and/or of binding human IL-4 in the presence of IL-4 Rα can be used in medicine, in diagnosis and in screening for agonists/antagonists of IL-13/IL-4. One such polypeptide is shown in FIG. 1.

8 Claims, 7 Drawing Sheets

FIG. 1A

```
GCC AAG GCT CCA GCC CGG CCG GGC TCC GAG GCG AGA GGC TGC ATG GAG TGG CCG GCG CGG
                                                                M   E   W   P   A   R
CTC TGC GGG CTG TGG GCG CTG CTG CTC TGC GCC GGC GGC GGG GGC GGG GGC GGG GGC GCC
 L   C   G   L   W   A   L   L   L   C   A   G   G   G   G   G   G   G   G   A
GCG CCT ACG GAA ACT CAG CCA CCT GTG ACA AAT TTG AGT GTC TCT GTT GAA AAC CTC TGC
 A   P   T   E   T   Q   P   P   V   T   N   L   S   V   S   V   E   N   L   C
ACA GTA ATA TGG ACA TGG AAT CCA CCC GAG GGA GCC AGC TCA AAT TGT AGT CTA TGG TAT
 T   V   I   W   T   W   N   P   P   E   G   A   S   S   N   C   S   L   W   Y
TTT AGT CAT TTT GGC GAC AAA CAA GAT AAG AAA ATA GCT CCG GAA ACT CGT CGT TCA ATA
 F   S   H   F   G   D   K   Q   D   K   K   I   A   P   E   T   R   R   S   I
GAA GTA CCC CTG AAT GAG AGG ATT TGT CTG CAA GTG GGG TCC CAG TGT AGC ACC AAT GAG
 E   V   P   L   N   E   R   I   C   L   Q   V   G   S   Q   C   S   T   N   E
AGT GAG AAG CCT AGC ATT TTG GTT GAA AAA TGC ATC TCA CCC CCA GAA GGT GAT CCT GAG
 S   E   K   P   S   I   L   V   E   K   C   I   S   P   P   E   G   D   P   E
TCT GCT GTG ACT GAG CTT CAA TGC ATT TGG CAC AAC CTG AGC TAC ATG AAG TGT TCT TGG
 S   A   V   T   E   L   Q   C   I   W   H   N   L   S   Y   M   K   C   S   W
CTC CCT GGA AGG AAT ACC AGT CCC GAC ACT AAC TAT ACT CTC TAC TAT TGG CAC AGA AGC
 L   P   G   R   N   T   S   P   D   T   N   Y   T   L   Y   Y   W   H   R   S
CTG GAA AAA ATT CAT CAA TGT GAA AAC ATC TTT AGA GAA GGC CAA TAC TTT GGT TGT TCC
 L   E   K   I   H   Q   C   E   N   I   F   R   E   G   Q   Y   F   G   C   S
TTT GAT CTG ACC AAA GTG AAG GAT TCC AGT TTT GAA CAA CAC AGT GTC CAA ATA ATG GTC
 F   D   L   T   K   V   K   D   S   S   F   E   Q   H   S   V   Q   I   M   V
AAG GAT AAT GCA GGA AAA ATT AAA CCA TCC TTC AAT ATA GTG CCT TTA ACT TCC CGT GTG
 K   D   N   A   G   K   I   K   P   S   F   N   I   V   P   L   T   S   R   V
AAA CCT GAT CCT CCA CAT ATT AAA AAC CTC TCC TTC CAC AAT GAT GAC CTA TAT GTG CAA
 K   P   D   P   P   H   I   K   N   L   S   F   H   N   D   D   L   Y   V   Q
TGG GAG AAT CCA CAG AAT TTT ATT AGC AGA TGC CTA TTT TAT GAA GTA GAA GTC AAT AAC
 W   E   N   P   Q   N   F   I   S   R   C   L   F   Y   E   V   E   V   N   N
AGC CAA ACT GAG ACA CAT AAT GTT TTC TAC GTC CAA GAG GCT AAA TGT GAG AAT CCA GAA
 S   Q   T   E   T   H   N   V   F   Y   V   Q   E   A   K   C   E   N   P   E
TTT GAG AGA AAT GTG GAG AAT ACA TCT TGT TTC ATG GTC CCT GGT GTT CTT CCT GAT ACT
 F   E   R   N   V   E   N   T   S   C   F   M   V   P   G   V   L   P   D   T
TTG AAC ACA GTC AGA ATA AGA GTC AAA ACA AAT AAG TTA TGC TAT GAG GAT GAC AAA CTC
 L   N   T   V   R   I   R   V   K   T   N   K   L   C   Y   E   D   D   K   L
TGG AGT AAT TGG AGC CAA GAA ATG AGT ATA GGT AAG AAG CGC AAT TCC ACA CTC TAC ATA
 W   S   N   W   S   Q   E   M   S   I   G   K   K   R   N   S   T   L   Y   I
ACC ATG TTA CTC ATT GTT CCA GTC ATC GTC GCA GGT GCA ATC ATA GTA CTC CTG CTT TAC
 T   M   L   L   I   V   P   V   I   V   A   G   A   I   I   V   L   L   L   Y
CTA AAA AGG CTC AAG ATT ATT ATA TTC CCT CCA ATT CCT GAT CCT GGC AAG ATT TTT AAA
 L   K   R   L   K   I   I   I   F   P   P   I   P   D   P   G   K   I   F   K
GAA ATG TTT GGA GAC CAG AAT GAT GAT ACT CTG CAC TGG AAG AAG TAC GAC ATC TAT GAG
 E   M   F   G   D   Q   N   D   D   T   L   H   W   K   K   Y   D   I   Y   E
AAG CAA ACC AAG GAG GAA ACC GAC TCT GTA GTG CTG ATA GAA AAC CTG AAG AAA GCC TCT
 K   Q   T   K   E   E   T   D   S   V   V   L   I   E   N   L   K   K   A   S
CAG TGA TGG AGA TAA TTT ATT TTT ACC TTC ACT GTG ACC TTG AGA AGA TTC TTC CCA TTC
 Q   *
```

```
TCC ATT TGT TAT CTG GGA ACT TAT TAA ATG GAA ACT GAA ACT ACT GCA CCA TTT AAA AAC
AGG CAG CTC ATA AGA GCC ACA GGT CTT TAT GTT GAG TCG CGC ACC GAA AAA CTA AAA ATA
ATG GGC GCT TTG GAG AAG AGT GTG GAG TCA TTC TCA TTG AAT TAT AAA AGC CAG CAG GCT
TCA AAC TAG GGG ACA AAG CAA AAA GTG ATG ATA GTG GTG GAG TTA ATC TTA TCA AGA GTT
GTG ACA ACT TCC TGA GGG ATC TAT ACT TGC TTT GTG TTC TTT GTG TCA ACA TGA ACA AAT
TTT ATT TGT AGG GGA ACT CAT TTG GGG TGC AAA TGC TAA TGT CAA ACT TGA GTC ACA AAG
AAC ATG TAG AAA ACA AAA TGG ATA AAA TCT GAT ATG TAT TGT TTG GGA TCC TAT TGA ACC
ATG TTT GTG GCT ATT AAA ACT CTT TTA ACA GTC TGG GCT GGG TCC GGT GGC TCA CGC CTG
TAA TCC CAG CAA TTT GGG AGT CCG AGG CGG GCG GAT CAC TCG AGG TCA GGA GTT CCA GAC
CAG CCT GAC CAA AAT GGT GAA ACC TCC TCT CTA CTA AAA CTA CAA AAA TTA ACT GGG TGT
GGT GGC GCG TGC CTG TAA TCC CAG CTA CTC GGG AAG CTG AGG CAG GTG AAT TGT TTG AAC
CTG GGA GGT GGA GGT TGC AGT GAG CAG AGA TCA CAC CAC TGC ACT CTA GCC TGG GTG ACA
GAG CAA GAC TCT GTC TAA AAA ACA AAA CAA AAC AAA ACA AAA CAA AAA AAC CTC TTA ATA
TTC TGG AGT CAT CAT TCC CTT CGA CAG CAT TTT CCT CTG CTT TGA AAG CCC CAG AAA TCA
GTG TTG GCC ATG ATG ACA ACT ACA GAA AAA CCA GAG GCA GCT TCT TTG CCA AGA CCT TTC
AAA GCC ATT TTA GGC TGT TAG GGG CAG TGG AGG TAG AAT GAC TCC TTG GGT ATT AGA GTT
TCA ACC ATG AAG TCT CTA ACA ATG TAT TTT CTT CAC CTC TGC TAC TCA AGT AGC ATT TAC
TGT GTC TTT GGT TTG TGC TAG GCC CCC GGG TGT GAA GCA CAG ACC CCT TCC AGG GGT TTA
CAG TCT ATT TGA GAC TCC TCA GTT CTT GCC ACT TTT TTT TTT AAT CTC CAC CAG TCA TTT
TTC AGA CCT TTT AAC TCC TCA ATT CCA ACA CTG ATT TCC CCT TTT GCA TTC TCC CTC CTT
CCC TTC CTT GTA GCC TTT TGA CTT TCA TTG GAA ATT AGG ATG TAA ATC TGC TCA GGA GAC
CTG GAG GAG CAG AGG ATA ATT AGC ATC TCA GGT TAA GTG TGA GTA ATC TGA GAA ACA ATG
ACT AAT TCT TGC ATA TTT TGT AAC TTC CAT GTG AGG GTT TTC AGC ATT GAT ATT TGT GCA
TTT TCT AAA CAG AGA TGA GGT GGT ATC TTC ACG TAG AAC ATT GGT ATT CGC TTG AGA AAA
AAA GAA TAG TTG AAC CTA TTT CTC TTT CTT TAC AAG ATG GGT CCA GGA TTC CTC TTT TCT
CTG CCA TAA ATG ATT AAT TAA ATA GCT TTT GTG TCT TAC ATT GGT AGC CAG CCA GCC AAG
GCT CTG TTT ATG CTT TTG GGG GGC ATA TAT TGG GTT CCA TTC TCA CCT ATC CAC ACA ACA
TAT CCG TAT ATA TCC CCT CTA CTC TTA CTT CCC CCA AAT TTA AAG AAG TAT GGG AAA TGA
GAG GCA TTT CCC CCA CCC CAT TTC TCT CCT CAC ACA CAG ACT CAT ATT ACT GGT AGG AAC
TTG AGA ACT TTA TTT CCA AGT TGT TCA AAC ATT TAC CAA TCA TAT TAA TAC AAT GAT GCT
ATT TGC AAT TCC TGC TCC TAG GGG AGG GGA GAT AAG AAA CCC TCA CTC TCT ACA GGT TTG
GGT ACA AGT GGC AAC CTG CTT CCA TGG CCG TGT AGA AGC ATG GTG CCC TGG CTT CTC TGA
GGA AGC TGG GGT TCA TGA CAA TGG CAG ATG TAA AGT TAT TCT TGA AGT CAG ATT GAG GCT
GGG AGA CAG CCG TAG TAG ATG TTC TAC TTT GTT CTG CTG TTC TCT AGA AAG AAT ATT TGG
TTT TCC TGT ATA GGA ATG AGA TTA ATT CCT TTC CAG GTA TTT TAT AAT TCT GGG AAG CAA
AAC CCA TGC CTC CCC CTA GCC ATT TTT ACT GTT ATC CTA TTT AGA TGG CCA TGA AGA GGA
TGC TGT GAA ATT CCC AAC AAA CAT TGA TGC TGA CAG TCA TGC AGT CTG GGA GTG GGG AAG
TGA TCT TTT GTT CCC ATC CTC TTC TTT TAG CAG TAA AAT AGC TGA GGG AAA AGG GAG GGA
AAA GGA AGT TAT GGG AAT ACC TGT GGT GGT TGT GAT CCC TAG GTC TTG GGA GCT CTT GGA
GGT GTC TGT ATC AGT GGA TTT CCC ATC CCC TGT GGG AAA TTA GTA GGC TCA TTT ACT GTT
TTA GGT CTA GCC TAT GTG GAT TTT TTC CTA ACA TAC CTA AGC AAA CCC AGT GTC AGG ATG
GTA ATT CTT ATT CTT TCG TTC AGT TAA GTT TTT CCC TTC ATC TGG GCA CTG AAG GGA TAT
GTG AAA CAA TGT TAA CAT TTT TGG TAG TCT TCA ACC AGG GAT TGT TTC TGT TTA ACT TCT
TAT AGG AAA GCT TGA GTA AAA TAA ATA TTG TCT TTT TGT ATG TCA AGC GGG CCG CCA CCG
CGG TGG AAA CTC CAG CTT
```

FIG. 1B

IL-13 AND IL-4 BINDING POLYPEPTIDES

FIELD OF THE INVENTION

The present invention relates inter alia to molecules capable of binding with human IL-13 and/or human IL-4.

BACKGROUND OF THE INVENTION

IL4 and IL13 are related cytokines that show a significant sequence identity [1,2] and share numerous biological activities. Both have been shown to be important in the induction of IgE and IgG4 synthesis in human B cells [3-6] and the differentiation of Th cells into a Th2 phenotype [8,11]. Among the events leading to IgE synthesis by B cells, induction of germline ε RNA transcription, which precedes the class switching to the corresponding H chain C region, has been shown to be triggered by IL4 and IL13 [6,9,10]. Th cells can be subdivided into two major subtypes according to their cytokine production capacities [11]. The major distinction between the two phenotypes are the capacity of Th1 cells to secrete IFNγ and Th2 cells to produce IL4 and IL5 [11]. Th2 cells are thought to be implicated in the development of atopy, allergy and some forms of asthma [12,13]. The differentiation of Th cells into the Th2 phenotype can be induced by IL4 [11]. IL13 was first considered as to be inactive on T cells [2]. However it has been shown recently to induce the differentiation of murine Th cells into the Th2 phenotype [8].

In addition to their effects on lymphocytes, IL4 and IL13 share the ability to inhibit the production of inflammatory cytokines by macrophages [1,2] and to up-regulate the expression of the vascular cell adhesion molecule-1 (VCAM-1) on endothelial cells [16,17,18] leading to adhesion and trans-endothelial migration of very late antigen 4 (VLA-4) expressing leukocytes [19]. This provides a basis for selective extravasation of eosinophils, the hallmark of the inflammatory pathology seen in allergy and asthma [20,58,59].

These two cytokines activate common cytokine receptor signaling pathways involving 4PS/IRS-1 [21–25] and the signal transducer and activator of transcription 6 (STAT-6; ref. 26–28). In the murine system, inactivation of STAT-6 has been demonstrated to affect both IL4 and IL13 signaling and to block IL4 and IL13-induced IgE synthesis or Th2 differentiation [29–31].

Studies have been conducted to examine if these two cytokines share a receptor or receptor subunits [2,18,32–34]. The IL4R is composed of two chains, the IL4Rα chain and the common γ chain ($\gamma_c$). The $\gamma_c$ is shared with the receptors of many of the other 4-helix bundle cytokines such as IL2, IL4, IL7, IL9 and IL15 [35,36]. The IL4Rα chain alone forms a tight complex with its ligand, whereas the $\gamma_c$ was thought to be mainly responsible for signal transduction. However, IL4- and IL-3-induced responses could be observed in cells which naturally do not express $\gamma_c$ or in lymphocytes obtained from severe combined immunodeficiency (SCID) patients who are deficient for $\gamma_c$ [34,37–39]. It has therefore been proposed that a second form of an IL4R exists which would be activated by both IL4 and IL13 (IL4R type II/IL13R; ref. 40).

A cDNA encoding for a human IL-13 receptor α chain (IL-13 R α) has been cloned (Caput et al [42]). IL-13 R α has been shown to participate in the type II IL-4 receptor which also contains an IL-4 R α chain.

SUMMARY OF THE INVENTION

The present inventors have now cloned from a human tissue source a cDNA encoding a polypeptide capable of binding human IL-13 which has not previously been identified. This polypeptide has only 27% sequence identity with the polypeptide identified by Caput et al. Furthermore the expression pattern of mRNAs encoding the molecule identified by the present inventors is very different from that of the molecule identified by Caput et al.

According to one aspect of the present invention there is provided a polypeptide which is capable of binding human IL-13 and/or of binding human IL-4 in the presence of IL-4 R α; which:

a) comprises the amino acid sequence shown in FIG. 1;

b) has one or more amino acid substitutions, deletions or insertions relative to a polypeptide as defined in a) above; or c) is a fragment of a polypeptide as defined in a) or b) above which is at least ten amino acids long and which is preferably at least fifty amino acids long.

DETAILED DESCRIPTION OF THE INVENTION

The term "polypeptide" is used herein in a broad sense to indicate that there are a plurality of peptide bonds present. It therefore includes within its scope substances which may sometimes be referred to in the literature as peptides, polypeptides or proteins.

It can be determined by using techniques known in the art whether or not a particular polypeptide is capable of binding human IL-13. For example, by binding the polypeptide to radiolabelled or tagged forms of human IL-13 or by competitive inhibition of the binding of radiolabelled or tagged forms of human IL-13 to its natural receptor. The binding affinity of the polypeptide for human IL-13 is preferably less than 10 μM, more preferably less than 1 μM (when determined at 37° C.).

Polypeptides within the scope of the present invention may be capable of binding human IL-4. This can also be determined by using techniques known to those skilled in the art. For example, by binding the polypeptide to radio-labelled or tagged forms of human IL-4 or by competitive inhibition of the binding of radiolabelled or tagged forms of human IL-4 to its natural receptor. The affinity of the polypeptide would be in the μM, ideally nM range.

Preferred polypeptides of the present invention form a moiety when combined with the IL-4 R α chain which is capable of binding IL-4 and/or IL-13. This moiety is within the scope of the present invention and is preferably membrane bound. It may represent a new form of IL-4 receptor (referred to herein as IL-4 type II receptor) and be useful in studying the structure and function of said receptor.

The polypeptides of the present invention which are capable of binding human IL-13 and/or human IL-4 are useful for a number of other purposes.

For example, they can be used to bind human IL-4 or human IL-13 and thereby to act as inhibitors by interfering with the interaction between human IL-13 or human IL-4 and their natural receptors. This is useful in medicine since it can be used in the treatment of diseases in which human IL-4 or human IL-13 are responsible (at least partially) for adverse effects in a patient. For example, polypeptides of the present invention could be used to inhibit IL-13 or IL-4 induced IgE synthesis in B cells. This is useful in the treatment of diseases where IgE or Th2 differentiation plays a role—e.g. in the treatment of atopy, atopic dermatitis, allergies, rhinitis, eczema, asthma or AIDS.

Polypeptides of the present invention may therefore be used in the treatment of a human or non-human animal. The treatment may be prophylactic or may be in respect of an existing condition. Examples of particular disorders which can be treated are discussed supra.

Thus a polypeptide of the present invention may be used in the manufacture of a medicament for the treatment of one or more disorders.

The medicament will usually be supplied as part of a pharmaceutical composition, which may include a pharmaceutically acceptable carrier. This pharmaceutical composition will usually be sterile and can be in any suitable form, (depending upon the desired method of administering it to a patient).

It may be provided in unit dosage form, will generally be provided in a sealed container, and can be provided as part of a kit. Such a kit is within the scope of the present invention. It would normally (although not necessarily) include instructions for use. It may include a plurality of said unit dosage forms.

Pharmaceutical compositions within the scope of the present invention may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such a composition may be prepared by any method known in the art of pharmacy, for example by admixing the active ingredient with a carrier under sterile conditions.

The pharmaceutical compositions may contain one or more of the following: preserving agents, solubilising agents, stabilising agents, wetting agents, emulsifiers, sweeteners, colourants, odourants, salts (substances of the present invention may themselves be provided in the form of a pharmaceutically acceptable salt), buffers, coating agents or antioxidants. They may also contain therapeutically active agents in addition to the substance of the present invention.

In addition to the medical uses, polypeptides of the present invention can be used in the production of diagnostic agents. For example they can be used in the production of antibodies which can in turn be used in the diagnosis of various disorders. Antibodies and their uses are discussed in greater detail below under the heading "Uses in raising or selecting antibodies".

The polypeptides themselves may be used for diagnosis. For example they could be used to diagnose the presence of mutated forms of IL-4 or IL-13 which do not bind to their natural receptors. This could be done by providing polypeptides of the present invention which act like a natural receptor in binding to wild-type human IL-4 or human IL-13 but which will not bind to mutated forms of IL-4 or IL-13 which do not bind to the corresponding natural receptor. As a positive control, wild type IL-4 or IL-13 could be used.

Polypeptides of the present invention can also be used in screening. (Substances identified as being useful for a given purpose by such screening are within the scope of the present invention when used or indicated as being useful for such a purpose.)

For example, polypeptides capable of binding IL-4 or IL-13 can be used to screen for substances capable of inhibiting the action of human IL-4 or human IL-13 (e.g. by competitive or non-competitive binding to the respective natural receptor). Such substances agents are useful in the treatment of the diseases discussed supra.

Alternatively, they can be used to screen for substances which act as agonists of human IL-4 or human IL-13.

Polypeptides of the present invention which bind human IL-4 or human IL-13 are therefore useful in screening for substances which could be useful in treating cancer or inflammatory diseases (e.g. rheumatoid arthritis and inflammatory bowel disease), multiple sclerosis. Alzheimer's disease, Lupus erythromatosus, thyroiditis, diabetes, uveitis, dermatitis, psoriasis, urticaria, nephrotic syndrome, glomerulonephritis, inflammatory bowel disease, ulcerative colitis, Crohn's disease, Sjogren's syndrome, toxoplasmosis, listeriosis, leprosy, Lyme disease, tuberculosis, malaria, leichmaniasis.

As will be appreciated by the skilled person, in some of the uses discussed above, polypeptides which can bind human IL-13 or human IL-4 but which does not necessarily have other functional regions, other than the IL-13 or IL-4 binding region can be used. Such polypeptides are therefore within the scope of the present invention.

Thus the polypeptides may be "soluble", i.e. in a form which enables them to be provided as extracellular polypeptides rather than membrane-bound polypeptides. Such polypeptides do not possess regions which would cause them to become anchored in a membrane. Thus they will generally not include hydrophobic domains which can give rise to the transmembrane regions in membrane-bound proteins. They will also generally not include regions which are normally located in the cytoplasm of a cell (e.g. regions involved in transmitting a cytoplasmic signal from a receptor following the binding of an interleukin to an extracellular part of that receptor—such regions are referred to herein as "signal transmitting regions".)

For example, the extracellular region of the polypeptide having the sequence shown in FIG. 1 (SEQ ID NO:8 and SEQ ID NO:9) could be used on its own as a soluble polypeptide capable of binding human IL-13 or human IL-4. Furthermore, one or more amino acid substitutions, insertions and/or deletions relative to said polypeptide could be made to provide other soluble polypeptides capable of binding human IL-13 or human IL-4. Indeed a skilled person could use protein binding studies to determine which part of said polypeptide is involved in binding human IL-13 and/or human IL-4. This could be done by scanning, directed or deletion mutagenesis, crosslinking with the ligands followed by protease digestion and sequencing, X-ray crystallography of the cytokine-receptor complex, epitope mapping of blocking antibodies, phage display libraries. Parts of the polypeptides having the sequence shown in FIG. 1 which are not involved in binding could therefore be identified and could be omitted when producing other polypeptides within the scope of the present invention.

One or more amino acid substitutions, deletions and/or insertions relative to said sequences may therefore be made in order to produce other polypeptides which may be capable of binding IL-4 or IL-13.

Soluble polypeptides of the present invention are likely to be especially useful in binding to IL-13 or IL-4 in a patient's circulatory system, thereby preventing bound IL-4 or IL-13 interacting with their receptors. Bound IL-4 or IL-13 could then be removed from a patient. For example immobilised antibodies having a high degree of specificity for the soluble polypeptides could be used. (It may however be possible to use membrane bound polypeptides for this and for the other purposes where soluble polypeptides are useful. For example liposomes comprising membrane bound polypeptides could be used. Like the polypeptides of the present invention they can flow with liquids and can therefore move through a patient's circulatory system. Such liposomes may even have advantages of their own—e.g. they can comprise a plurality of polypeptides of the present invention and can therefore be highly effective due to being "multivalent" for polypeptides of the present invention.)

The soluble polypeptides of the present invention could be used in treating the diseases discussed above in which IL-4 or IL-13 are at least partially responsible for adverse effects in a patient (these diseases are discussed supra) since they can be easily introduced into a patient's circulatory system and bind to IL-4 or IL-13.

They can also be used for screening purposes.

In some circumstances however it may be preferred to use polypeptides of the present invention which include in addition to an IL-13 or IL-4 binding region at least a signal transmitting region (e.g. where it is desired to screen for substances), e.g. agonists, capable of producing an IL-13 or IL-4 mediated response). In these circumstances membrane bound polypeptides will usually be particularly preferred.

It should be noted that the present invention is not limited to polypeptides which bind to IL-4 or IL-13 or to uses thereof. According to a further aspect of the present invention there is provided a polypeptide comprising a signal transmitting region (which can be involved in providing the intracellular signals in response to IL-4 or IL-13 binding to a receptor). Such a polypeptide can be used for screening purposes.

For example, it could be used in screening for substances which might inhibit signalling via an IL-13 or IL-4 receptor in vivo by preventing the action of cytoplasmic signalling molecules, e.g. kinases, STATs, IRS-1 or IRS-2 (IRS-1 and IRS-2 are discussed by Sun et al in Nature 377:173–177 (1995)). Alternatively it could be used to screen for substances which stimulate or improve such signalling in vivo.

An example of a polypeptide which could be used in such a manner is the polypeptide comprising the 59 amino acid cytoplasmic sequence of the polypeptide given in FIG. 1 (amino acids 368 to 427). Of course, one or more amino acid insertions, deletions or substitutions could be made relative to such a polypeptide to produce other polypeptides comprising a signal transmitting region. For example, a series of deletions could be made to identify the smallest part of the polypeptide consisting of the 59 amino acid sequence discussed above which could be used in screening. Such a part would also be a polypeptide within the scope of the present invention.

One or more amino acid substitutions and/or insertions could then be made to such a polypeptide to produce other polypeptides having a signal transmitting region. Such polypeptides would also be useful in screening.

Whatever polypeptides with a signal transmitting region are used, they are preferably provided in phosphorylated form. Desirably the tyrosine residues are phosphorylated. This can be achieved by treating the polypeptide with kinases or expressing them in cells or bacteria expressing appropriate kinases. Alternatively phosphopeptides can be synthesized chemically.

Whatever the nature of polypeptides of the present invention, they can be used in raising or selecting antibodies. The present invention therefore includes antibodies which bind to a polypeptide of the present invention. Preferred antibodies bind specifically to polypeptides of the present invention and can therefore be used to purify such polypeptides.

The antibodies described in the foregoing paragraph are within the scope of the present invention. They may be monoclonal or polyclonal.

Polyclonal antibodies can be raised by stimulating their production in a suitable animal host (e.g. a mouse, rat, guinea pig, rabbit, sheep, goat or monkey) when a polypeptide of the present invention is injected into the animal. If necessary an adjuvant may be administered together with the substance of the present invention. The antibodies can then be purified by virtue of their binding to a polypeptide of the present invention.

Monoclonal antibodies can be produced from hybridomas. These can be formed by fusing myeloma cells and spleen cells which produce the desired antibody in order to form an immortal cell line. Thus the well known Kohler & Milstein technique (Nature 256 52–55 (1975)) or variations upon this technique can be used.

Techniques for producing monoclonal and polyclonal antibodies which bind to a particular polypeptide are now well developed in the art. They are discussed in standard immunology textbooks, for example in Roitt et al. *Immunology* second edition (1989). Churchill Livingstone, London.

In addition to whole antibodies, the present invention includes derivatives thereof which are capable of binding to polypeptides of the present invention. (The sections of this application which refer to antibodies therefore apply mutatis mutandis to derivatives thereof, unless the context indicates otherwise.)

Thus the present invention includes antibody fragments and synthetic constructs. Examples of antibody fragments and synthetic constructs are given by Dougall et al in *Tibtech* 12 372–379 (September 1994).

Antibody fragments include inter alia Fab, F(ab')$_2$ and Fv fragments (these are discussed in Roitt, et al [supra], for example).

Fv fragments can be modified to produce a synthetic construct known as a single chain Fv (scFv) molecule. This includes a peptide linker covalently joining $V_h$ and $V_l$ regions which contribute to the stability of the molecule.

Other synthetic constructs which can be used include CDR peptides. These are synthetic peptides comprising antigen binding determinants. Peptide mimetics may also be used. These molecules are usually conformationally restricted organic rings which mimic the structure of a CDR loop and which include antigen-interactive side chains.

Synthetic constructs include chimaeric molecules, Thus, for example. humanised (or primatised) antibodies or derivatives thereof are within the scope of the present invention. An example of a humanised antibody is an antibody having human framework regions, but rodent hypervariable regions.

Synthetic constructs also include molecules comprising an additional moiety which provides the molecule with some desirable property in addition to antigen binding. For example the moiety may be a label (e.g. a fluorescent or radioactive label).

Alternatively, it may be a pharmaceutically active agent.

The antibodies or derivatives thereof of the present invention have a wide variety of uses. They can be used in purification and/or identification of polypeptides of the present invention. Thus they may be used in diagnosis.

For example, they can be used to evaluate the level of expression of IL-13 and/or IL-4 receptors in a given sample or to evaluate the pattern of expression in different cells or tissues. Abnormal levels or patterns of expression may be indicative of a disorder.

Such antibodies can be used to identify differences in IL-13 or IL-4 receptors which arise due to allelic variation between individuals in a population. This is useful in the identification of particular allelic variants which are associated with a given disease.

Antibodies against polypeptides of the present invention are also useful in identifying IL-13 or IL-4 receptors or parts thereof which have been shed from cells (as may occur in certain diseases) such as cancer, leukaemia, atopy, atopic dermatitis, allergies, rhinitis, eczema, asthma, AIDS, Lupus erythromatosus, thyroiditis, diabetes, uveitis, dermatitis, psoriasis, urticaria, nephrotic syndrome, glomerulonephritis, inflammatory bowel disease, ulcerative colitis, Crohn's disease, Sjogren's syndrome, toxoplasmosis.

Antibodies are also useful in purification of polypeptides of the present invention. Preferred antibodies therefore have a high degree of specificity for polypeptides of the present invention.

The antibodies or derivatives thereof of the present invention can be provided in the form of a kit for screening for the polypeptides of the present invention.

Preferred Polypeptides of the Present Invention

From the foregoing discussions it will be appreciated that the present invention includes many polypeptides within its scope and that these polypeptides can be useful for a number of different purposes. Preferred polypeptides of the present invention are particularly useful for these purposes and can be identified as having substantial amino acid sequence identity with one or more of the following amino acid sequences:

a) the complete amino acid sequence shown in FIG. 1 (amino acids 1 to 427),
b) the cytoplasmic amino acid sequence shown in FIG. 1 (amino acids 368 to 427),
c) the extracellular amino acid sequence shown in FIG. 1 (amino acids 27 to 347).

Such polypeptides may have at least 50% amino acid sequence identity with one of the above. More preferably the degree of sequence identity is at least 60% or at least 70%. Most preferably the degree of sequence identity is at least 80% (e.g. at least 90%, at least 95% or at least 99%).

The degree of amino acid sequence identity can be calculated, for example, using a program such as "bestfit" (Smith and Waterman, Advances in Applied Mathematics, 482–489 (1981)) to find the best segment of similarity between any two sequences. The alignment is based on maximising the score achieved using a matrix of amino acid similarities, such as that described by Schwarz and Dayhof (1979) Atlas of Protein Sequence and Structure. Dayhof, M. O. Ed pp 353–358.

Where high degrees of sequence identity are present there may be relatively few differences in amino acid sequence. Thus for example there may be less than 20 differences, less than 10 differences, or even only 1 amino acid difference.

The skilled person is in a position to provide useful preferred polypeptides with substantial amino acid sequence identity to the sequences given above since the skilled person is aware that one or more amino acid substitutions, insertions and/or deletions can often be made relative to a given sequence without losing desired characteristics (e.g. the capability of binding to human IL-4 or human IL-13 and/or the possession of a signal transmitting region.

The polypeptides of the present invention may be produced by techniques known to those skilled in the art. For example gene cloning techniques may be used to provide a nucleic acid sequence encoding such a polypeptide. By using an appropriate expression system (e.g. a eukaryotic, prokaryotic or cell free system) the polypeptide can then be produced. It can then be purified using standard purification techniques.

Alternatively, chemical synthesis techniques may be used to produce polypeptides of the present invention. Such techniques generally utilise solid phase synthesis. Chemical synthesis techniques which allow polypeptides having particular sequences to be produced have now been automated. Machines capable of chemically synthesising polypeptides are available, for example, from Applied Biosystems Ltd.

Various modifications which can be made to a specified polypeptide sequence will now be discussed.

A polypeptide may consist of a particular amino acid sequence, or may have an additional N-terminal and/or an additional C-terminal amino acid sequence.

Additional N-terminal or C-terminal sequences may be provided for various reasons. Techniques for providing such additional sequences are well known in the art. These include using gene cloning techniques to ligate nucleic acid molecules encoding polypeptides or parts thereof, followed by expressing a polypeptide encoded by the nucleic acid molecule produced by ligation.

Additional sequences may be provided in order to alter the characteristics of a particular polypeptide. This can be useful in improving expression or regulation of expression in particular expression systems. For example, an additional sequence may provide some protection against proteolytic cleavage. This has been done for the hormone Somatostatin by fusing it at its N-terminus to part of the β galactosidase enzyme (Itakwa et al., Science 198: 105–63 (1977)).

Additional sequences can also be useful in altering the properties of a polypeptide to aid in identification or purification.

For example, a polypeptide may be linked to a moiety capable of being isolated by affinity chromatography. The moiety may be a pre-selected antigen or an epitope and the affinity column may comprise immobilised antibodies or immobilised antibody fragments which bind to said antigen or epitope (desirably with a high degree of specificity). The fusion protein can usually be eluted from the column by addition of an appropriate buffer.

Additional N-terminal or C-terminal sequences may, however, be present simply as a result of a particular technique used to obtain a substance of the present invention and need not provide any particular advantageous characteristic.

One or more substitutions, deletions and/or insertions may be made relative to a specified polypeptide (which itself may include heterologous N-terminal and/or C-terminal, as discussed above). These are discussed below:

(i) Substitutions

The skilled person is aware that various amino acids have similar properties. One or more such amino acids of a polypeptide can often be substituted by one or more other such amino acids without eliminating a desired characteristic of that polypeptide.

For example, the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic).

Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains).

Substitutions of this nature are often referred to as "conservative" or "semi-conservative" amino acid substitutions.

(ii) Deletions

Amino acid deletions can be advantageous since the overall length and the molecular weight of a polypeptide can be reduced whilst still retaining a desired characteristic. This can enable the amount of polypeptide required for a particular purpose to be reduced. For example if the polypeptide is to be used in medicine, dosage levels can be reduced by using such polypeptides.

(iii) Insertions

Amino acid insertions relative to a given polypeptide sequence can be made e.g. to assist in identification, purification or expression: as explained above in relation to fusion proteins.

Polypeptides incorporating amino acid changes (whether substitutions, deletions or insertions) relative to the sequence of a polypeptide as defined in a) above can be provided using any suitable techniques. For example, a nucleic acid sequence incorporating a desired sequence change can be provided by site directed mutagenesis. This can then be used to allow the expression of a polypeptide having a corresponding change in its amino acid sequence.

Nucleic Acid Molecules

In addition to the polypeptides of the present invention and antibodies/antibody derivatives discussed above, the present invention also provides nucleic acid molecules.

Such nucleic acid molecules:

a) code for a polypeptide according to the present invention: or b) are complementary to molecules as defined in a) above: or c) hybridise to molecules as defined in a) or b) above.

These nucleic acid molecules and their uses are discussed in greater detail below:

The polypeptides of the present invention can be coded for by a large variety of nucleic acid molecules, taking into account the well known degeneracy of the genetic code. All of these molecules are within the scope of the present invention.

They can be inserted into vectors and can be cloned to provide large amounts of DNA or RNA for further study. Suitable vectors may be introduced into host cells to enable the expression of polypeptides of the present inventions using techniques known to the person skilled in the art. Alternatively, cell free expression systems may be used.

Techniques for cloning, expressing and purifying polypeptides are well known to the skilled person. Various techniques are disclosed in standard text books such as in Sambrook et al [*Molecular Cloning* 2nd Edition, Cold Spring Harbor Laboratory Press (1989)]; in Old & Primrose [*Principles of Gene Manipulation* 5th Edition, Blackwell Scientific Publications (1994); and in Stryer [*Biochemistry* 4th Edition, W H Freeman and Company (1995)].

By using appropriate expression systems different forms of polypeptides of the present invention may be expressed.

For example, the polypeptide may be provided in glycosylated or non-glycosylated form. Non-glycosylated forms can be produced by expression in prokaryotic hosts, such as *E. coli,* whereas glycosylated forms can be produced in eukaryotic hosts, such as *S cerevisiae.*

Polypeptides comprising N-terminal methionine may be produced using certain expression systems, whilst in others the mature polypeptide will lack this residue.

Polypeptides may initially be expressed to include signal sequences. Different signal sequences may be provided for different expression systems. Alternatively signal sequences may be absent.

Polypeptides may be expressed with or without hydrophobic domains which can be used in anchoring polypeptides in a cell membrane. Where it is desired to produce soluble polypeptides, such hydrophobic domains will not be present.

In addition to nucleic acid molecules coding for substances according to the present invention (referred to herein as "coding" nucleic acid molecules), the present invention also includes nucleic acid molecules complementary thereto. Thus, for example, each strand of a double stranded nucleic acid molecule is included within the scope of the present invention in addition to the double stranded molecule itself. Also included are mRNA molecules and complementary DNA molecules (e.g. cDNA molecules).

Nucleic acid molecules which can hybridise to any of the nucleic acid molecules discussed above are also covered by the present invention. Such nucleic acid molecules are referred to herein as "hybridising" nucleic acid molecules. Hybridising nucleic acid molecules can be useful as probes or primers, for example.

Nucleic acid molecules may therefore be useful as in the analysis of allelic variation. One example of this is in the use of such molecules in identifying allelic variation in a region of a nucleic acid molecule encoding the signal peptide part of polypeptides according to the present invention.

The signal peptide area contains a long polyglycine stretch. The mRNA segment encoding for this poly G stretch forms GC reach repeats. The present inventors have observed deletions in this area when the cDNA was subjected to multiple cycles of polymerization (PCR) and believe that this region could lead to instability which would be a source of allelic variation. Allelic variation in this area could affect the expression of the IL-13 receptor and be involved in pathologies associated with disregulation of the IgE synthesis or T helper cell differentiation in the TH1–TH2 phenotype, such as an allergy. (This sequence area is not present in the murine counterpart.) Probes or primers which are poly G and or G-C rich molecules (or which are polyA or C-G rich in the case of complementary strands) are therefore particularly useful.

Desirably hybridising molecules of the present invention are at least 10 nucleotides in length and preferably are at least 25 or at least 50 nucleotides in length. The hybridising nucleic acid molecules may specifically hybridise to nucleic acids which code for a polypeptide of the present invention or which are complementary to nucleic acids molecules which code for a molecule of the present invention.

Preferred hybridising molecules hybridise to such molecules under stringent hybridisation conditions. One example of stringent hybridisation conditions is where attempted hybridisation is carried out at a temperature of from about 35° C. to about 65° C. using a salt solution which is about 0.9 molar. However, the skilled person will be able to vary such parameters as appropriate in order to take into account variables such as probe length, base composition, type of ions present, etc.

In addition to being used as probes, hybridising nucleic acid molecules of the present invention can be used as antisense molecules to alter the expression of substances of the present invention by binding to complementary nucleic acid molecules. This technique can be used in antisense therapy. Such molecules may also be used to produce ribozymes. Ribozymes can be used to regulate expression by binding to and cleaving RNA molecules which include particular target sequences.

A hybridising nucleic acid molecule of the present invention may have a high degree of sequence identity along its length with a nucleic acid molecule which codes for a polypeptide of the present invention or which is complementary to a nucleic acid molecule which codes for a polypeptide of the present invention (e.g. at least 50%, at least 75% or at least 90% sequence identity). As will be appreciated by the skilled person, the higher the sequence identity a given single stranded nucleic acid molecule has with another nucleic acid molecule, the greater the likelihood that it will hybridise to a nucleic acid molecule which is complementary to that other nucleic acid molecule under appropriate conditions.

In view of the foregoing description the skilled person will appreciate that a large number of nucleic acids are within the scope of the present invention.

Unless the context indicates otherwise, nucleic acid molecules of the present invention may have one or more of the following characteristics:

1) they may be DNA or RNA;
2) they may be single or double stranded;
3) they may be provided in recombinant form i.e. covalently linked to a 5' and/or a 3' flanking sequence to provide a molecule which does not occur in nature;
4) they may be provided without 5' and/or 3' flanking sequences which normally occur in nature;
5) they may be provided in substantially pure form (thus they may be provided in a form which is substantially free from contaminating proteins and/or from other nucleic acids);
6) they may be provided with introns (e.g. as a full length gene) or without introns (e.g. as cDNA).

The present invention will now be described, by way of example only, with reference to the accompanying drawings.

BRIEF DESCRIPTION OF THE DRAWINGS

FIG. 1 shows the nucleotide sequence SEQ ID NO: 8 and deduced amino acid sequence SEQ ID NO: 9 of the insert of the cDNA clone 3.1. The putative signal and transmembrane region are indicated using bolt characters. The WSXWS SEQ ID NO: 2 motif is underlined. The GC rich region of the cDNA is underlined double (see Example 1).

The examples are provided below and are followed by a "Materials and Methods" section which explains some of the techniques used in greater detail.

EXAMPLE 1

Cloning of a human IL-13 R chain.

To obtain a probe we searched the Gene Bank expressed sequence tag (EST) data base with the sequence of the extracellular protein domain of a known murine IL-13 receptor (IL-13 R) chain. (The cloning of said chain is disclosed in Hilton et al, *PNAS* 93:497 (1996)). The sequence of two ESTs (H57074 and H89334) with reading frames which encode peptides with a high degree of sequence identity to the murine IL-13 R chain were used to design PCR oligonucleotide primers. These primers were used to amplify a segment of the human IL-13 R cDNA from activated tonsilar B cell cDNA (see Materials and Methods). This human IL-13 R cDNA fragment was used to screen a λgt10 library of activated tonsilar B cell cDNA and to clone a human IL-13 R cDNA. Sequencing of the largest cDNA insert obtained from the screening revealed a 4 Kb mRNA sequence with an open reading frame encoding for a 427 amino acid polypeptide (FIG. 1). The deduced polypeptide includes two hydrophobic regions likely to represent a signal peptide and a transmembrane domain. The transmembrane domain is followed by a 59 amino acid cytoplasmic region. Interestingly this region contains a YXXQ (SEQ ID NO:1) sequence motif which has been identified as a consensus for STAT binding (ref. 56). The extracellular domain includes the four cystein residues and WSXWS (SEQ ID NO:2) motif conserved among the type-I cytokine receptor superfamily (ref. 43).

The deduced polypeptide sequence of human IL-13 R has 26% sequence identity to the IL-5 receptor α chain and has 27% sequence identity to the human IL-13 receptor recently cloned from the human Caki-1 cell line by Caput et al (*J. Biol. Chem.* 271: 16921 (1996)) which is referred to as IL-13 R α2 herein. The human IL-13 receptor cloned by the present inventors is referred to herein as IL-13 R α1 since it is believed to be a different α chain than the α chain cloned from the human Caki-1 cell line.

EXAMPLE 2

IL-13 R α1 chain mRNA is expressed in a large panel of organs.

Figure 2:
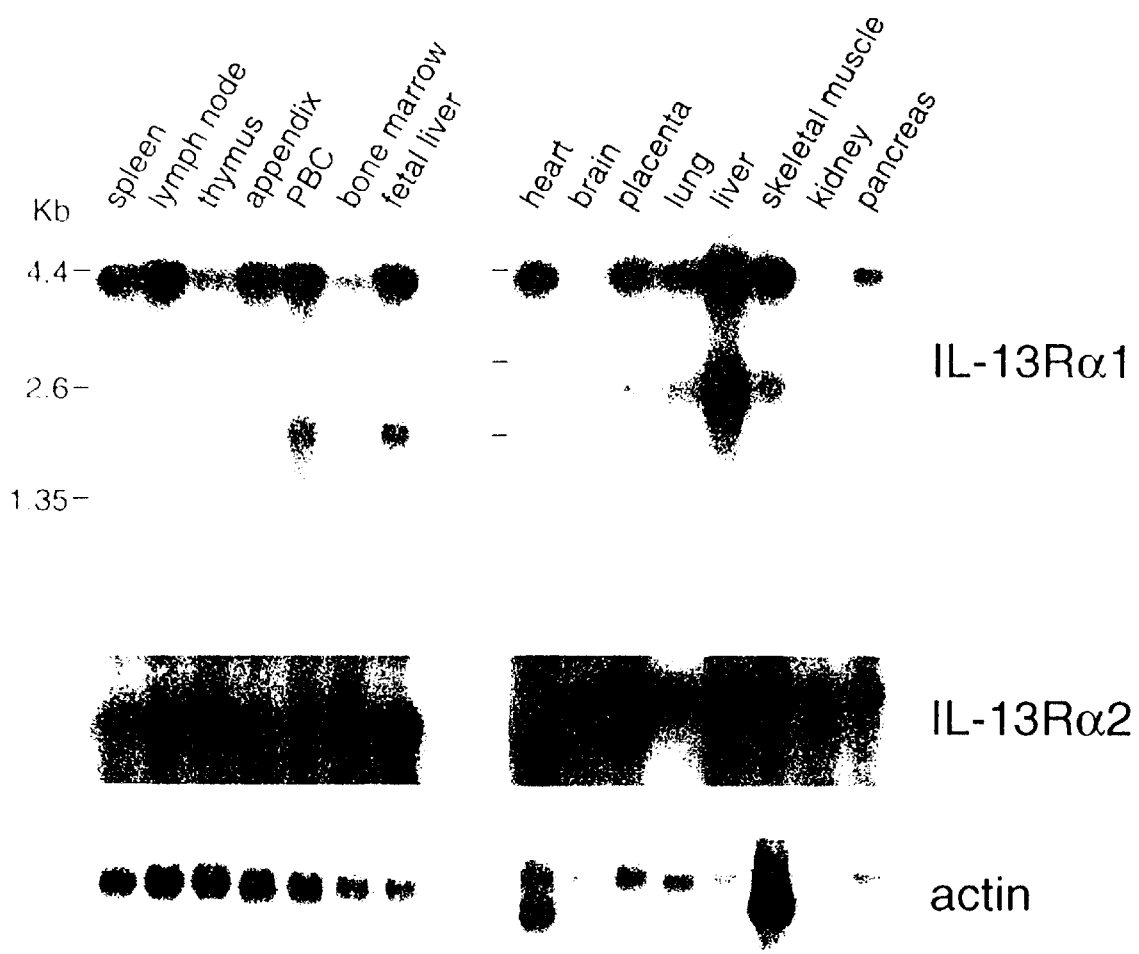
FIG. 2 shows the Northern blot analysis of IL-13 R α1 and IL-13 R α2 mRNA in human organ and tissues. Poly A$^+$ RNA blots were hybridized with cDNA probes for IL-13 R α1, IL-13 R α2 or actin mRNA. The autoradiography exposure time: IL-13 R α1 , 18 h; IL-13 R α2, 7 days; actin. 3 h (see Example 2).

We studied the steady state level of IL-13 R α1 chain mRNA in human organs by Northern blot assay using commercially available Poly A⁺ RNA blots (FIG. 2). Two major classes of mRNA were hybridizing with the IL-13 R α1 cDNA probe; a band of 4.2 Kb and a doublet around 2 Kb. The apparent molecular weight of the largest RNA species is close to the size of the cloned cDNA. In the Northern blot assays, we used a short segment of the open reading frame of the cloned cDNA which should be conserved in any RNA encoding for the IL-13 R α1 receptor.

The Northern blot assay hybridization signal for the small molecular weight RNA species was nevertheless much lower than the one obtained for the 4.2 Kb mRNA. This suggests that the 4.2 Kb mRNA represents the predominant species (FIG. 2).

The IL-13 R α1 mRNA steady state levels were highest in liver. It was low in brain and kidney (FIG. 2). When studied in lymphoid organs and peripheral blood leukocytes, the highest expression was in the spleen, lymph nodes, appendix and PBL and the lowest in bone marrow and thymus. This indicates that the level of the mRNA encoding the IL-13 R α1 chain is higher in organs containing a larger fraction of mature lymphocytes, with the exception of the liver in which expression was high in both adult and fetal poly A⁺ RNA.

Expression of the mRNA coding for IL-13 R α2, was studied by using a cDNA probe corresponding to the entire open reading frame described by Caput et al (ref. 42). The signal in Northern blot was much lower than that for IL-13 R α1. However, the expression of a 1.7 Kb IL-13 R α2 mRNA could be detected in the poly A⁺ RNA from all organs tested. The highest steady state levels were detected in placenta and liver. Among the lymphoid organs and peripheral blood leukocytes, the IL-13 R α2 chain mRNA level was the highest in thymus, bone marrow and fetal liver. For comparison, the same blots were rehybridized with a control actin probe (FIG. 2).

In comparison, the transcript expression pattern of the IL-13 R α1 and α2 reveals a differential expression pattern in the studied organs with strong differences in thymus, bone marrow (primary lymphoid organs), brain and kidney.

EXAMPLE 3

The expression of IL-13 R α1 mRNA can be detected in a variety of primary cells and cell lines.

Figure 3A:
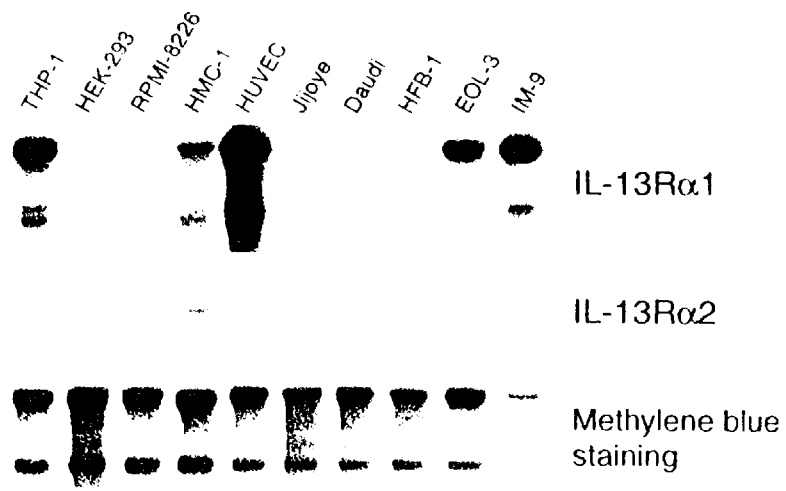
FIGS. 3A–3C show the Northern blot analysis of IL-13 R α1 and IL-13 R α2 mRNA in primary human cells and cell lines (panel A), B cells and cell lines (panel B) and T cells and T cell clones (panel C). Total RNA (poly A$^+$ when specified in the figure) was isolated from the indicated cells. The Northern blot assay was performed with 2 µg RNA aliquots except for RNA isolated from peripheral T cell for which 1 µg aliquots were used. Peripheral T cells and JY were subjected to the indicated stimulation before RNA isolation. The membranes were stained with methylene blue (lower panel) and hybridized with the cDNA probes for IL-13 R α1 or IL-13 R α2. Autoradiography exposure time: IL-13 R α1, 24 h; IL-13 R α2, 7 days (see Examples 3, 4, 5).

We compared the steady state levels of the IL-13 R α1 chain in total RNA isolated from a panel of cells and cell lines by Northern blot. Interestingly, this mRNA was detectable in HUVEC cells, synovial cells, chondrocytes, the monocytic cell line THP-1, the immunoglobulin secreting lymphoblast cell line IM-9, the immature mast cell line HMC-1 and the eosinophilic cell line Eol-3 (FIG. 3A). No signal could be detected with Northern blot in total RNA isolated from the adenovirus transformed human embryonic kidney cell line 293, the Burkitt lymphoma cell lines Jijoye and Daudi and the B cell line HFB-1. When identical parallel Northern blots were hybridised with an IL-13 R α2 cRNA probe, a signal was detected in RNA isolated from synovial cells, chondrocytes and the immature mast cell line HMC-1.

EXAMPLE 4

IL-13 receptor cel chain is expressed by B cells.

The IL-13 R α1 cDNA was cloned from a tonsilar B cells library using a probe obtained by RT-PCR from RNA isolated from the same cells. Expression in B cells was therefore expected. A hybridization signal could be detected in a Northern blot assay using a cRNA probe on total B cell RNA (FIG. 3B).

Figure 3B:
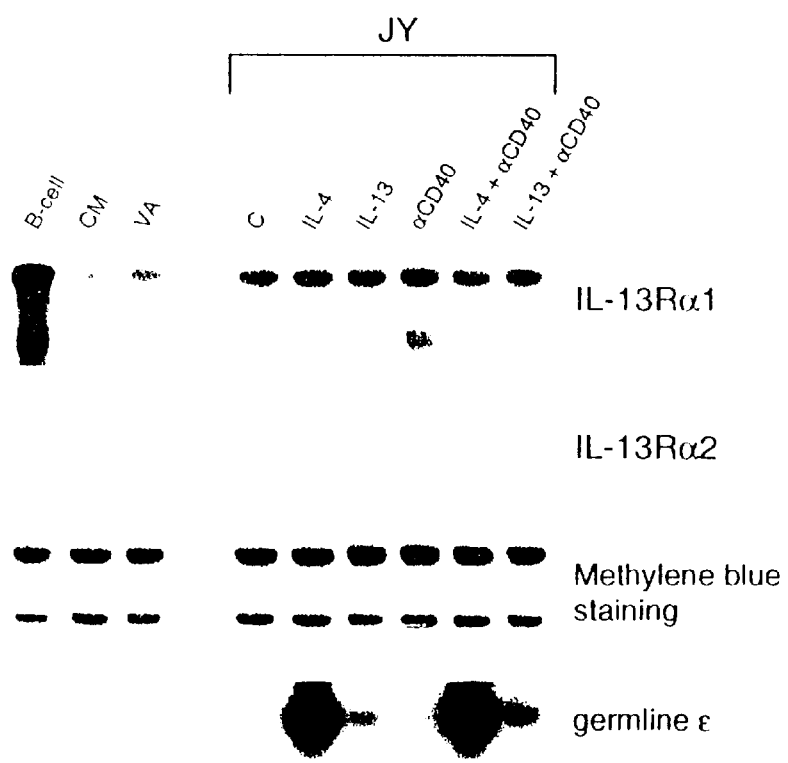

We observed in previous studies that JY is a B cell line in which easily detectable germline ε transcript synthesis can be induced by either IL-4 or IL-13 (ref. 57 and FIG. 3B). We examined if this capacity to respond to both IL-4 and IL-13 was paralleled by the expression of the IL-13 R α1 mRNA. As shown in FIG. 3B. IL-13 R α1 mRNA was indeed detectable by Northern blot in this cell line (FIG. 3B). It was not affected by the stimulation conditions used to induce germline ε transcript synthesis (FIG. 3B).

EBV transformed B cell line from SCID patients deficient for $\gamma_c$ or JAK-3 were used to study the role of this IL-4 receptor type I chain and the kinase associated to it in the induction of germline ε response by IL-4 and IL-13 (ref. 39; Gauchat et al, manuscript submitted for publication). Results indicated that a JAK-3 and $\gamma_c$ independent response to IL-4 could be observed and that these two proteins were unlikely to be involved in the induction by IL-13 of a germline ε transcripts response. A simple interpretation from these data was that the response observed in the SCID patient cell lines is involving an IL-4 type II/IL-13 receptor which would not comprise $\gamma_c$ and would not signal through JAK-3. We therefore used Northern blot assays to study if IL-13 R α1 chain expression could be detected in the SCID patient B cell lines. As shown in FIG. 3B, IL-13 R α1 chain mRNA was detectable in the EBV transformed cell from the SCID patients tested, VA ($\gamma_c$ deficient) and CM (JAK-3 deficient).

The IL-13 R α2 cDNA probe was also obtained from tonsilar B cell cDNA, indicating that this mRNA is expressed in these cells. The signal observed was however at the limit of detection of the Northern blot assay, even when this assay was performed using a high specific activity riboprobe (FIG. 3B). No signal could be detected in the JY B cell line or in the cell lines from the SCID patients VA or CM (FIG. 3B) or B cell lines from normal donors (data not shown).

EXAMPLE 5

IL-13 receptor α1 chain mRNA is expressed in T cells.

Figure 3C:
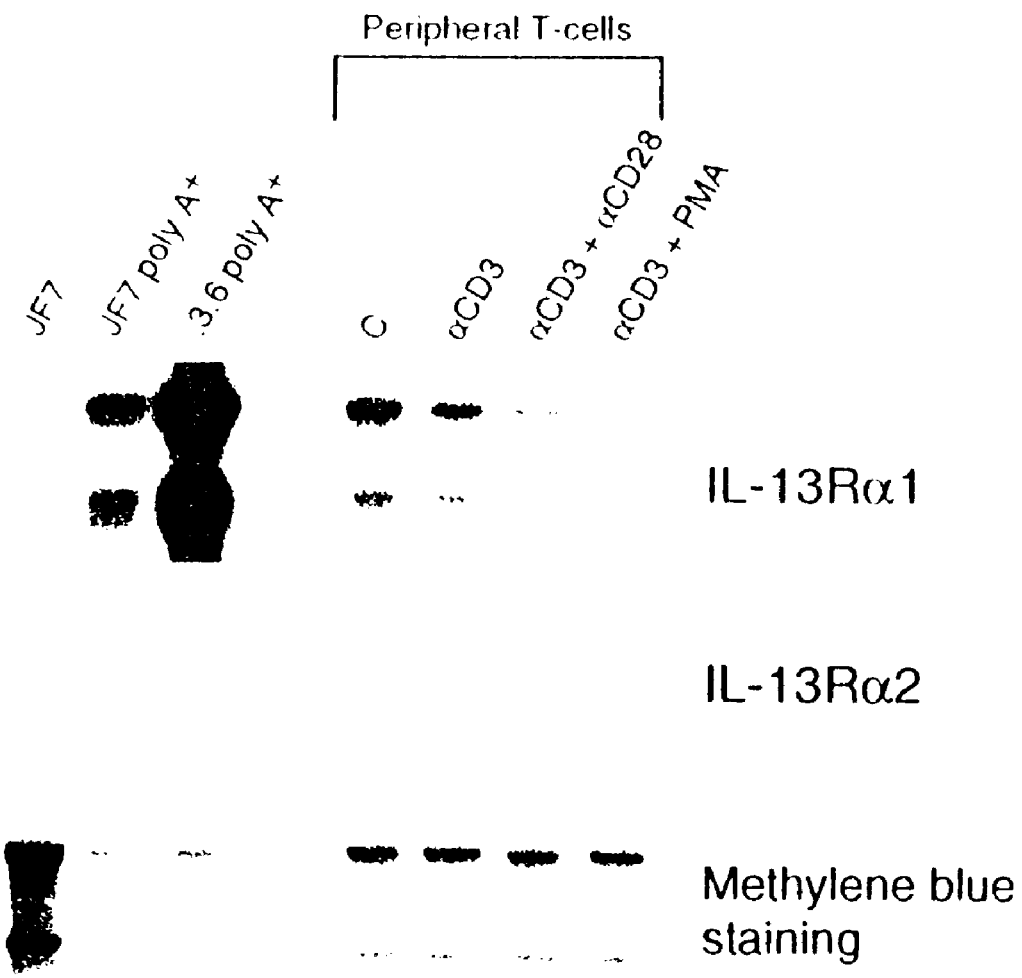

Whereas initial studies on IL-13 indicated that T cells were not responding to this cytokine (ref. 2), recent studies in mouse have shown that IL-13 could induce a Th2 T cell differentiation (ref. 14). We therefore studied IL-13 R α1 and α2 mRNA expression in T cells (FIG. 3C). The IL-13 R α1 mRNA could clearly be detected in the CD4⁺ T cell clones JF7 and MAB PHA .3.6. This observation was not restricted to T cell clones but could be extended to peripheral blood T cells (FIG. 3C). In the peripheral T cells we failed to observe up-regulation of the IL-13 R α1 mRNA level in response to mitogenic stimulation. This included stimulation by immobilized anti-CD3 alone or used in conjunction with phorbol esters or anti-CD28 for 4 h (data not shown) or 16 h (FIG. 3C) and by Ionomycin and phorbol esters or the lectin concanavalin A (data not shown). When identical parallel blots were subjected to hybridization with the IL-13 R α2 cRNA probe, no signal could be detected, even with poly A⁺ RNA isolated from the T cell clones (FIG. 3C and data not shown).

EXAMPLE 6

Cross-competition between IL4 and IL13 for the heterologous IL4/IL13R complex.

Figure 4:
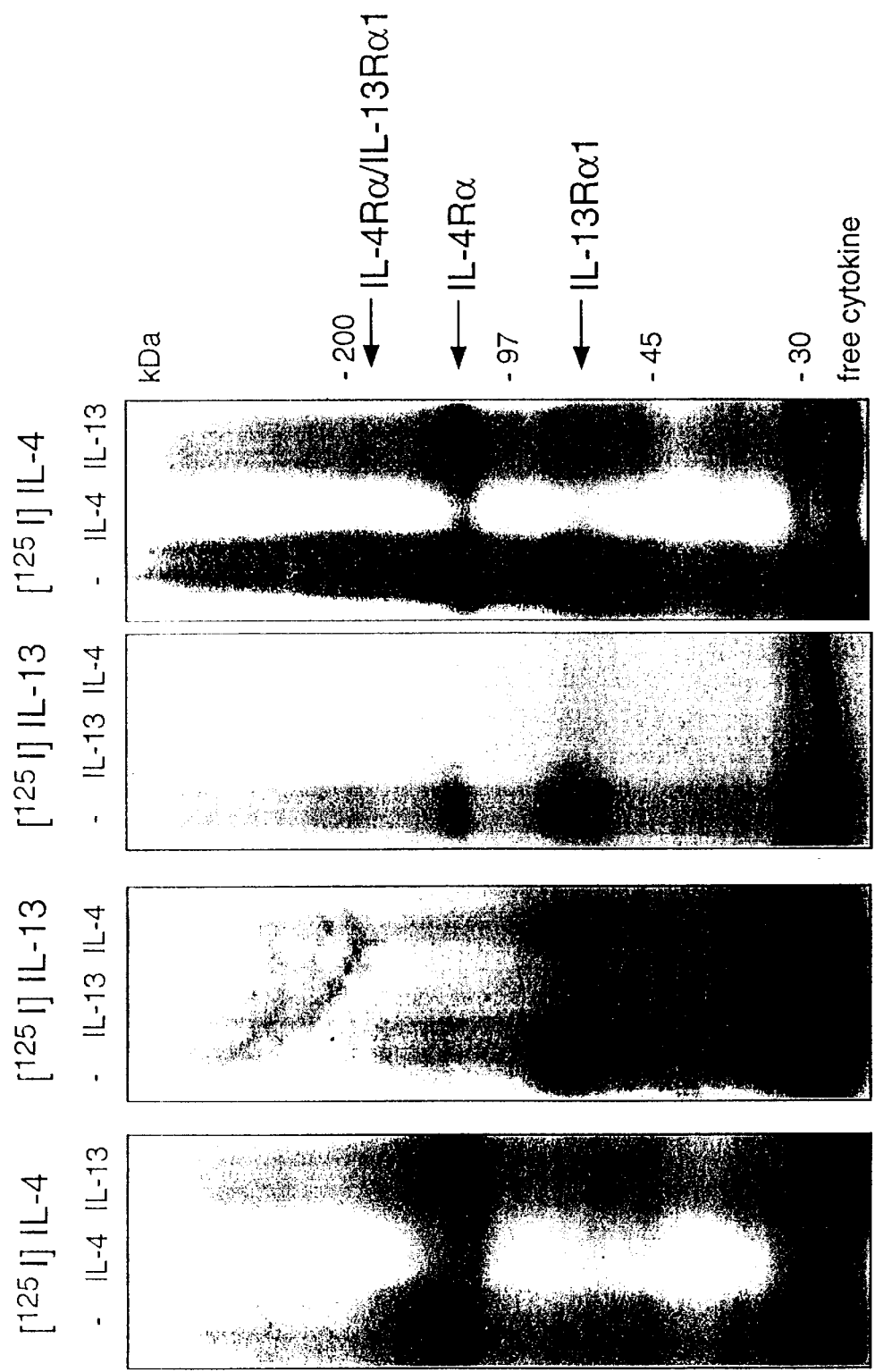
FIGS. 4A–4C show radioligand affinity cross-linking of IL4 and IL13 to IL4Rα and IL13Rα1 transfectants. COS7 cells transiently transfected either with the cDNA of the human IL4Rα (A), the human IL13 Rα1 (B) or both (C) were detached and labeled with 0.5 nmol/L of [$^{125}$I]IL4 or 3 nmol/L of [$^{125}$I]IL13 as indicated. Displacement of the radioiodinated ligand was performed with a 1000 fold excess of unlabeled cytokine or with buffer (−) before cross-linking was performed using 2.5 mmol/L disuccinimidyl suberate. The lysates were analyzed under reducing conditions on a gradient (3–10%) SDS-PAGE, and exposed to X-ray films for 1–3 days. Net molecular masses of the receptors (R) were calculated by subtracting 19 kDa for bound IL4 or 15 kDa for bound IL13 (see Example 6).

The cDNAs of human IL13Rα1 and I-4Rα were transiently transfected in COS7 cells either individually or together in order to characterize the cloned human IL13Rα1 alone or in the context of a coexpressed IL14Rα chain. Expression of both cDNAs led to functional expression of IL4 and IL13Rα1 (FIG. 4A). Radioligand cross-linking of iodinated IL4 to COS7 cells expressing the IL4Rα chain showed binding to a 130 kDa protein (FIG. 4B). This binding was competed by cold IL4 but not by IL13. Cross-linking of iodinated IL13 to COS7 cells expressing the cloned IL13Rα1 chain resulted in binding of IL13 to a protein migrating as a double band at 65–75 kDa. Iodinated IL13 was displaced by an excess of unlabeled IL13 but not by IL-4 at the same concentration. Untransfected COS7 cells expressed very low levels of IL4R and IL13R (data not shown). Coexpression of both receptors in COS7 cells generated a receptor complex which supported cross-competition of [$^{125}$I] IL13 by 1000 fold excess cold IL13 and IL4 from both receptors (FIG. 4B). In the case of [$^{125}$I] IL4, excess cold IL4 displaced labeled IL4 from both receptors. In contrast, excess cold IL13 could displace labeled IL4 from the IL13Rα1 receptor but only to a very limited degree from the IL4Rα chain.

EXAMPLE 7

IL13 binding studies.

To address the issue of whether the IL13Rα1 confers similar binding properties as reported for its mouse homologue. COS7 cells were transiently transfected with a plasmid containing the IL13Rα1 cDNA. In radioligand binding assays IL13 bound with low affinity (KD=1.4±0.4 nM Table 1). Similarly. COS7 cells transfected with IL4Rα bound IL4 with a KD equal to 0.9±0.4 nM. In co-transfection experiments with IL4Rα and IL13Rα1, a limited number of high affinity receptors for IL4 (KD=32±14 pM: 300±100 receptors/cell) and IL13 (KD=50±20 pM: 500±200 receptors/cell) were observed. The majority of IL4 and IL13 bound with low affinity to the co-transfected cells expressing 15.000±3.000 IL4R/cell with an affinity of 2–3 nM and 45.400±15.500 IL-13R/cell with a KD of 2–6 nM.

TABLE 1

Binding parameters of IL-4 and IL-13 to transfected COS7 cells.

| Transfection | Ligand | KD (pM) | R$_{max}$ | R/cell |
|---|---|---|---|---|
| IL13Rα1 | IL13 | 1,430 ± 360 | 5.8 10$^{-11}$ | 3,620 ± 1,010 |
| IL4Rα1 | IL4 | 870 ± 430 | 9.4 10$^{-11}$ | 6,100 ± 4,700 |
| IL13Rα1 + IL4Rα1 | IL4 | 2,460 ± 640 | 2.6 10$^{-10}$ | 15,180 ± 2,530 |
|  |  | 31.5 ± 14.2 | 3.9 10$^{-12}$ | 240 ± 108 |
| IL13Rα1 + IL4Rα1 | IL13 | 6,290 ± 3,020 | 7.3 10$^{-10}$ | 45,450 ± 15,450 |
|  |  | 45.9 ± 22.5 | 7.4 10$^{-12}$ | 460 ± 220 |

Figure 5:
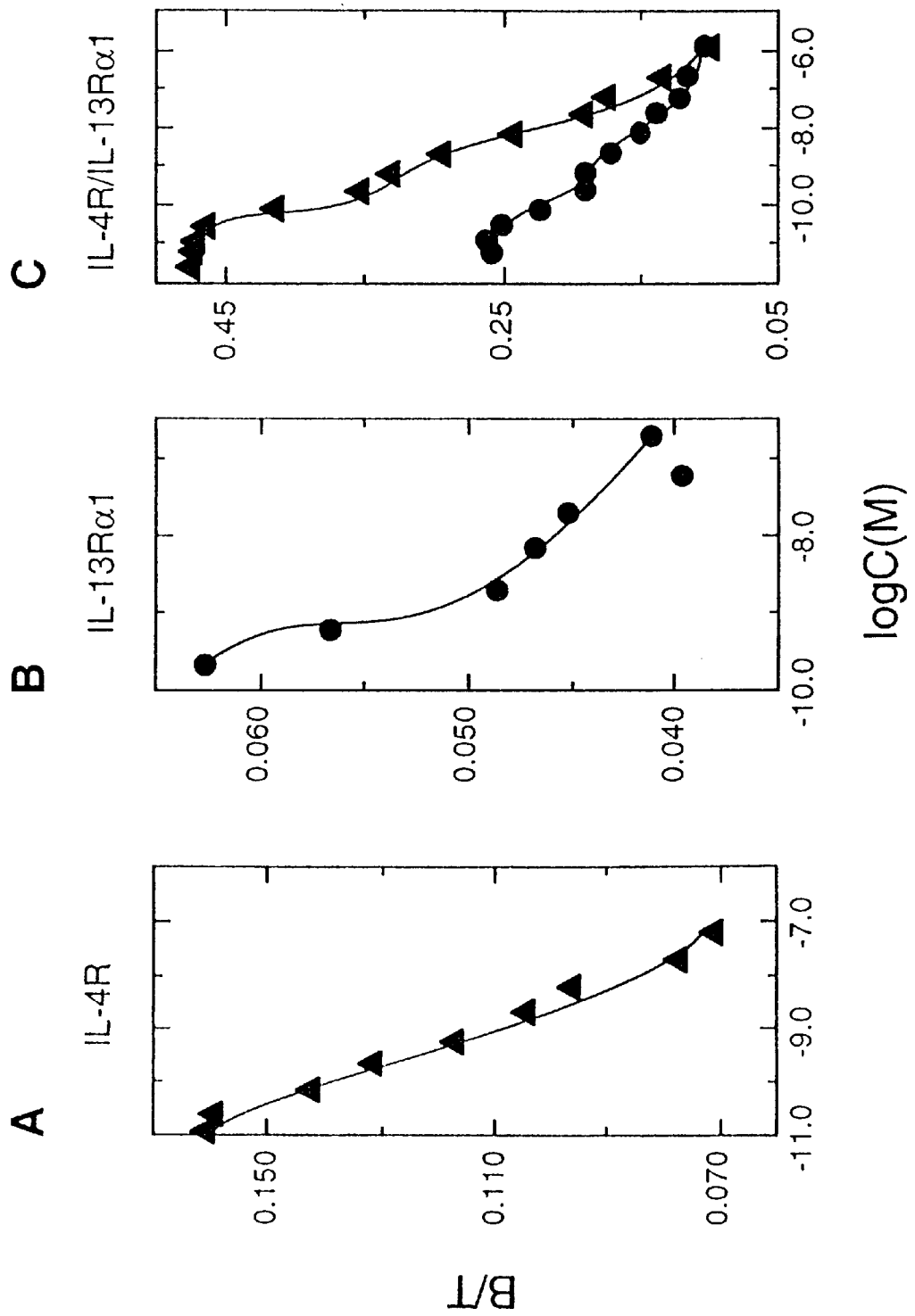
FIGS. 5A–5C show binding of radiolabeled IL4 and IL13 to IL4Rα and IL13Rα1 transfectants. Receptor binding analysis of radiolabeled IL4 (▲) and IL13 (●) was performed with COS7 cells transiently transfected with (A) the cDNA of either the human IL4Rα (full line), the IL13Rα1 (dashed line) or (B) cotransfected with both cDNAs. Data were analyzed with the computerized weighted least-square curve fitting software described by [7] (see Example 7).

Binding study results are illustrated in FIG. 5.

Discussion

The signal peptide area of IL-13 R α1 contains a long poly glycine stretch. The mRNA segment encoding for this poly G stretch forms GC reach repeats. We observed deletions in this area when the cDNA was subjected to multiple cycles of polymerization (PCR). Observations suggest that the GC repeats might lead to allelic variations. Variations in this region of the protein might therefore result in changes of receptor surface expression related to allergy or atopy.

IL-13 R α1 cDNA encodes a protein binding IL-13 when transiently transfected in the monkey kidney cell lines Cos. When expressed in conjunction with IL-4 R α1 chain, it forms a receptor for both IL-4 and IL-13 indicating that it could be implicated in the type II IL-4 receptor (ref. 40). Consistent with previous reports indicating that this type II IL-4/IL-13 receptor is γ$_c$ independent, the IL-13 R α1 chain did not form an IL-4 receptor when expressed in conjunction with γ$_c$ in transiently transfected cells. We tested if IL-13 R α could bind IL-5. We observed no IL-5 binding to IL-13-R α1 when it was expressed alone or in conjunction with IL-5 R β in Cos transfectants.

We have compared the expression of the mRNA encoding IL-13 R α1 and α$^2$ in RNA purified from organs, leukocytes and cell lines using Northern blot assay. Expression of the IL-13 R α1 and α2 where both ubiquitous indicating that they are expressed by cells present in all organs tested. The variation in the steady state levels of the two mRNAs were not parallel. This suggests that the two receptor mRNA steady state levels are not coregulated and that the two receptors might have different functions. Among the organs of the immune system tested, the expression of the IL-13 R α1 was high in the organ with large proportion of mature leukocytes and lower in the organs in which selection and differentiation of immature lymphocytes predominate.

When the study was extended to primary and transformed cells, the IL-13 Rα1 mRNA was detected in B cells, T cells, transformed endothelial cells as well as monocytic, eosinophilic and immature mast cells lines. The pattern of expression observed is therefore compatible with a role of IL-13 Rα1 as a receptor mediating the effects of IL-13 which have been described on B, T and endothelial cells [6, 14, 16–18]. The mRNA encoding IL-13 Rα2 chain could only be detected in purified tonsillar B cells, in chondrocytes, synovial cells and the immature mast cell line HMC-1, indicating a more restricted pattern of expression or lower steady state levels which would prevent the detection using Northern blot assay even the sensitivity obtained with very high specific activity cRNA probes.

The mRNA encoding IL-13 R α1 was also detected in B cell lines from γ$_c$ deficient SCID patients in which a type I IL-4 receptor independent IL-4 and IL-13 response can be detected. No signal for IL-13 R α2 mRNA was observed. This is data is therefore compatible with IL-13 R α1 acting for a receptor subunit involved in a type II IL-4/IL-13 receptor transducing IL-4 and IL-13 signalling in the absence of γ$_c$ in B cells (ref. 40).

Materials and Methods

Cells and Tissue Cultures. The mast cell line HMC-1 was from Dr. Butterfield (Rochester, Minn.) and was maintained in Dulbeco's modified Eagle's medium and Ham's F-12 nutrient solution. The source and culture conditions of the cell lines EOL-3, HFB-1, JY and the human T cell clones JF7 and MAB. PHA .3.6 have been described previously (44–46). The EBV transformed B cell lines from the JAK-3 deficient SCID patient CM (47) and γc deficient X-SCID patient VA were obtained from Dr. L. D. Notarangelo (University of Brescia, Italy) and maintained in RPMI 1640 supplemented with 10% fetal calf serum. The cell lines COS7, HEK-293, RPMI-8226, Jijoye, Daudi and IM-9. were obtained from American Type Culture Collection (Rockville, Md.) and cultured according to their specification. Tonsilar B cells were isolated from tonsilar mononuclear cells by depleting the T cells by rosetting with sheep red blood cells. The purified B cell preparation used were more that 98% CD20$^+$. Peripheral blood T cells were purified from healthy subject peripheral blood mononuclear cells by rosetting. The preparations used contained more than 95% CD3$^+$ cells. T cells were cultured in RPMI 1640 medium supplemented with 10% heat-inactivated AB$^+$ human serum (CTS, Annemasse, France) and stimulated with 10 μg/ml immobilized anti-CD3 (Immunotech, Marseille, France) alone or in combination with 10 μg/ml immobilized anti-CD28 (Immunotech) or phorbol myristate acetate (10 nM). Human umbilical vein endothelial cells were harvested and expanded as described (18).

Cloning of human IL-13 R α1 chain cDNA:

The Gene Bank EST data base was searched using the murine IL-13 R α. extracytoplasmic domain protein sequence as query. Two EST with open reading frames with high degrees of amino acid identity were identified (EST H57074 and H89334). The EST sequence was used to design the PCR primers
CTGAGCTACATGAAGTGTTCTTGGCTCCCT (SEQ ID NO:3) and
CAGAGTTTGTCATCCTCATAGCATAACTTA (SEQ ID NO:4) and the probe
AATACCACTCCCGACACTAACTATACTCTC (SEQ ID NO:5).

Poly A+ RNA was isolated from tonsillar B cell incubated for 5 days in the presence of rIL-4 (200 U/ml) and anti-CD40 mAb (1 μg/ml) using the guanidium thiocyanate-CsTFA procedure (ref. 48) followed by two cycles of oligo (dT)-cellulose chromatography. Oligo dT primed cDNA was synthesized using SuperScript II reverse transcriptase (Life Technologies AG. Basel, Switzerland) according to the instructions of the supplier and used as template for the PCR reactions performed with AmpliTaq polymerase (Perlin Elmer. Rotkreuz, Switerland). The amplification product which hybridized with the radiolabelled probe was then cloned into the vector pCRII using a TA cloning kit (Invitrogen BV. Leek, The Netherland) and analised by DNA seqencing. Double stranded cDNA was synthesized according to the instructions of the reverse transcriptase supplier. ligated to NotI-EcoRI adaptors (Pharmacia LKB Biotechnology, Uppsala, Sweden), size selected by chromarography on Sephacry S 400 spun collumn (Pharmacia LKB) and cloned in the EcoR I site of λgt10. One million clones of the amplified cDNA library (library size: 1.4×10$^6$ independent cDNAs)were screened using the human IL-13 R α1 chain cDNA fragment isolated from the pCRII vector and labelled with $^{32}$P by random hexamer priming (ref. 49). 15 independent clones were isolated by multiple screening cycles. The cDNA of the three largest inserts were recloned in pBluescript II SK (Stratagene GMBH, Zürich, Switzerland). The largest cDNA (named 3.1) was fully sequenced. For this purpose, pBluescript 3.1 was digested with the restriction enzymes ApaI and EcoRI and deletion mutants were obtained using and Exo-Mung deletion kit (Stratagene). The 3.1 cDNA and 31 deletion mutants were sequenced using an ABI sequencer (Perkin-Elmer). The sequencing data were then assembled into a single continuous sequence. The sequencing of the second strand and the editing of the first strand sequence were performed using oligonucleotide primers.

Subcloning of the human IL-13 receptor α1, IL-4 R α and γ$_c$ cDNA in the expression vector pCDLSRα 296:

A segment of cDNA 3.1 containing the openreading frame was isolated from the vector pBluescript II SK with the restriction enzymes NotI and XbaI. Restriction the cDNA fragment was made blunt end using T4 polymerase and recloned between the Pst I and Kpn restriction sites of the expression vector pCDLSRα296 (ref. 50) rendered blunt end using the same DNA polymerase. The IL-4Rα cDNA was isolated from pBSKS-hIL-4R (ref. 51, kind gift of Dr. J.-P. Galizzi, Schering-Plough Immunology Laboratory, Dardilly, France) using the restriction enzymes EcoRV and NcoI. The insert was rendered blunt end and recloned in pCDLSRα 296 as described for the IL-13 R α1 cDNA. The γ$_c$ cDNA was exised from the plasmid pIL-2R2γ2 using the restriction enzyme Xba I (ref. 52, kind gift of Dr. H. Asao, Tohoku University School of Medicine, Sendai, Japan) rendered blunt end and recloned in pCDLSRα 296 as described for the IL-13 α1 chain cDNA.

Detection of the IL-13 receptor α1 and α2 chain mRNA by Northern blot assay:

We used either cDNA or cRNA probes for the dectection of IL-13 receptor α1 and α2 chain mRNA. IL-13 receptor α1 chain [$^{32}$P]-labelled cDNA pobes were obtained by labelling the XmnI-ScaI restriction fragment of the cDNA by random hexamer priming (ref. 49). To produce a cRNA probe specific for IL-13 receptor α1 chain the same fragment was recloned in the EcoRV site of pBluescript II SK and used for the transcription of a [$^{32}$P]-labelled probe (ref. 53). To produce probes specific for the IL-13 receptor α2 chain, the cDNA was amplified by PCR from the tonsilar B cell cDNA used previously for the cloning of the α1 chain cDNA, using the primers
GGAGAAATGGCTTTCGTTTGCTTGGCTATC (SEQ ID NO:6) and
TACCATGTCTCTTGATATGGAAAGTCTTCA (SEQ ID NO:7).

The cDNA was cloned in the pCRII vector. cDNA probes were labelled with [$^{32}$P] by random hexamer priming (ref. 49). cRNA probes labelled with [$^{32}$P] were generated by transcribing the region in 3' of the cDNA insert EcoRV restriction site (ref. 53).

Total RNA was isolated either by the guanidium thiocyanate-CsCl procedure (ref. 48) or using TRIzol (Life technologies) according to the instructions of the manufacturer. For some experiments, Poly A$^+$ RNA was isolated by one cycle of oligo (dT)-cellulose chromatography.

The Human Immune System Multiple Tissue Northern blot and the Human Multipie Tissue Northern blot (Clontech) where hybridized with the IL-3R α1 or α2 and with actin cDNA (ref. 54) probes in ExpressHyb Hybridization Solution (Clontech) according to the instruction of the Northern blot manufacturer. For the other Northern blot assays, aliquots of RNA were subjected to electrophoresis in 1% agarose. 6% formalindhyde gels, electrotransferred to Nylon+ membranes and fixed by UV irradiation (ref. 55). Hybridization with cRNA probes and washing conditions were the same as described previously (ref. 55). The wash cycles included a digestion with ribonuclease A. which prevents rehybridisation of the RNA blots with a control probe. Therefore, membranes were stained with methylene blue to localize and quantify rRNA before hybridization.

Transfection of Cos cells with the IL-13 receptor, IL-4 receptor and γ$_c$ cDNA:

To transfect construct with the cDNA or empty vector in Cos cells cells were electroporated in 20 mM HEPES pH 7.4. 150 mM NaCl with aliquots of DNA (25 Mg). Electroporation condition were; 260V, 960 μF and ∞ resistance. Binding studies were performed 48 h after transfection.

Affinity cross-linking of [$^{125}$I]IL-4 and [$^{125}$I]IL-13 to their cognate receptors.

Iodination of recombinant IL-4 and IL-13 was performed as recently described (18). Transfected COS7 cells were detached by incubating cells in phosphate-buffered saline (PBS) containing 1 mM EDTA and resuspended in MEM Apha medium (Life Technologies) containing 1% bovine serum albumin (BSA). Aliquots of 200 μl containing 2×10$^6$ cells were incubated on ice with 0.5 nM [$^{125}$I]IL-4 or 3 nM[$^{125}$I]IL-13. For competition, excess unlabelled ligand (1 mM) was added 20 min prior to the iodinated cytokines. The cross-linking procedure was performed as described (18) and samples were analyzed by SDS-polyacrylamide gel electrophoresis under reducing conditions using (w/v) polyacrylamide gels. Autoradiography was performed at −70° C., exposing X-ray Hyperfilms (Amersham International) for 3 days.

Ligand binding studies.

Cells were harvested as described above and used in binding assays as described earlier (18). Receptor binding data were determined by displacing iodinated ligand by either cold IL-4 or IL-13 and analyzing the obtained data.

REFERENCES

1. Minty, A., Chalon, P., Derocq, J.-M., Dumont. X., Guillemot, J.-C., Kaghat, M., Labit, C., Leplatois, P., Liauzun, P., Miloux, B., Minty, C., Casellas, P., Loison. G., Lupker, J., Shire, D., Ferrara, P. & Caput, D. (1993) *Nature* (London) 362, 248–250.
2. Zurawski, S., Vega, Jr. F., Hughe, B. & Zurawski, G. (1993) *EMBO J.* 12, 2663–2670.
3. Lebman, D. A. & Coffman, R. L. (1988) *J. Exp. Med* 168,853.
4. Pené, J., Rousset, F., Briére, F., Chrétien, I., Bonnefoy, J.-Y., Spits, H., Yokota, T., Arai, N., Arai, K.-I., Banchereau, J. & de Vries, J. E. (1988) *Proc. Natl. Acad. Sci. USA* 85, 6880-
5. Gascan, H., Gauchat, J.-F. Roncarolo, M.-G. Yssel, H., Spits, H. & de Vries, J. E. (1991) *J. Exp. Med.* 173, 747–750.
6. Punnonen, J., Aversa, G., Cocks, B. G., McKenzie, A. N. J., Menon, S., Zurawski, G., de Waal Malefyt, R. & de Vries, J. E. (1993) *Proc. Natl. Acad. Sci. USA* 90, 3730–3734.
7. Porrelli, R. N., Munson, P. J. and Rodbard, D. *J. Recept. Res.* 1993 13: 6.
8. Kuna, P., Reddigari, S. R., Schall, T. J., Rucinski, D., Viksman, M. Y. and Kaplan, A. P., *J. Immunol.* 1992. 149: 636.
9. Rothman, P., Lutzker, S., Cook, W., Coffman, R. & Alt, F. (1988) *J. Exp. Med.* 168, 2385-
10. Gauchat, J.-F., Lebman, D., Coffman, R. L., Gascan, H. & de Vries, J. E. (1990) *J. Exp. Med.* 172, 463–473.
11. Mosmann, T. R. & Coffman, R. L. (1989) *Annu. Rev. Immunol.* 7, 145–173.
12. Robinson, D. S., Hamid, Q., Ying, S., Tsicopoulos, A., Barkans, J., Bentley, A. M., Corrigan, C., Durham, S. R. & Kay, A. B. (1992) *New. Engl. J. Med.* 326, 298–304.
13. Kapsenberg, M. L., Jansen, H. M. Bos, J. D. & Wierenga, E. A. (1992) *Curr. Op. Immunol.* (1992) 4, 788–793.
14. Kaplan, M. H., Schindler, U., Smiley, S. T. & Grusby, M. J. (1996) *Immunity* 4, 313–319.
15. Schleimer, R. P., Sterbinsky, S. A., Kaiser, J. Bickel, C. A., Klunk, D. A., Tomioka, K., Newman, W., Luscinskas, F. W., Gimbrone, M. A. Jr., McIntire, B. W. & Bochner, B. S. (1992) *J. Immunol.* 148, 1086-
16. Sironi, M., Sciacca, L. F., Matteucci, C., Conni, M., Vecci, A., Bernasconi, S., Minty, A., Caput, D., Ferrara, P., Collota, F. & Mantovadi, A. (1994) *Blood* 84, 1913-
17. Bochner, B. S., Klunk, D. A., Sterbinsky, S. A. Coffman, R. L. & Scheimler, R. P. (1995) *J. Immunol.* 154, 799–803.
18. Schnyder, B., Lugli, S., Feng, N., Etter, H., Lutz, R. A., Ryffel, B., Sugamura, K., Wunderli-Allenspach, H. & Moser, R. (1996) *Blood* 87, 4286–4295.
19. Elices, M. J., Osborn, L., Takada, Y., Crouse, C., Luhowskyj S., Hemler, M. E. & Lobb, R. R. (1990) *Cell* 60, 577-
20. Seminaro, M. C. & Gleich, G. J. (1994) Curr. Opin. Immunol. 6, 860-
21. Wang, L. M., Keegan, A. D., Li, W., Lienhard, G. E., Pacini, S., Gutkind, J. S., Myers, M. G. Jr., Sun, X. J., White, M. F., Aaronson, S. A., Paul, W. E. & Pierce, J. H. (1993) *Proc. Natl. Acad. Sci. USA* 90, 4032–4036.
22. Sun, X. J., Wang, L. M., Zhang, Y., Yenush, L., Myers, M. G. Jr., Glasheen, E., Lane, W. S., Pierce, J. H. & White, M. F. (1995) *Nature* (London) 377, 173–177.
23. Welham, M. J., Learmonth, L., Bone, H. & Schrader, J. W. (1995) *J. Biol. Chem.* 270, 12286–12296.
24. Keegan, A. D., Johnston, J. A., Tortolani, P. J., McReynolds, L. J., Kinzer, C., O'Shea, J. J. & Paul, W. E. (1995) *Proc. Natl. Acad. Sci. USA* 92, 7681–7685.
25. Wang, L.-M., Michieli, P., Lie, W.-R., Liu, F., Lee, C.-C., Minty, A., Sun, X.-J., Levine, A., White, M. F. & Pierce. J. H. (1995) *Blood* 86, 4218–4227.
26. Kotanides, H. & Reich, N. C. (1983) *Science* 262, 1265–1267.
27. Schindler, C., Kashleva, H., Pernis, A., Pine, R. & Rothman, P. (1994) *EMBO J.* 13, 1350–1356.
28. Hou, J., Schindler, U., Henzel, W. J., Ho, T. C., Brasseur, M. & McKnight, S. L. (1994) *Science* 265, 1701–1706.
29. Kaplan, M. H., Schindler, U., Smiley, S. T. & Grusby, M. J. (1996) Immunity 4, 313–319.
30. Takeda, K., Tanaka, T., Shi, W., Matsumoto, M., Minami, M., Kashiwamura, S., Nakanishi, K., Yoshida, N., Kishimoto, T. & Akira, S. (1996) *Nature* (London) 380, 627–630.
31. Shimoda, K., van Deursen, J., Sangster, M. Y., Sarawar, S. R., Carson, R. T., Tripp, R. A., Chu, C., Quelle, F. W., Nosaka, T., Vignali, D. A. A., Doherty, P. C., Grosveld, G., Paul W. E. & Ihle, J. N. (1996) *Nature* (London) 380, 630–633.
32. Zurawski, S. M., Chomarat, P., Djossou, O., Bidau, C., McKenzie, A. N., Miossec, P., Banchereau, J. & Zurawski, G. (1995) *J. Biol. Chem.* 270, 13869–13678.
33. Lefort, S., Vita, N., Reeb, R., Caput, D. & Ferrara, P. (1995) *FEBS Lett.* 366, 122–126.
34. Obiri, N. J., Debinski, W., Leonard, W. J & Puri, R. K. (1995) *J. Biol. Chem.* 270, 8797–8804.
35. Kondo, M., Takeshita, T., Ishii, N., Nakamura, M., Watanabe, S., Arai, K. & Sugamura, K. (1993) *Science* 262, 1874-
36. Nogushi, M., Nakamura, Y., Russel, S. M. Ziegler, S. F., Tsang, M., Cao, X. & Leonard, W. J. (1993) *Science* 262, 1877-
37. Lin, J.-X., Migone, T.-S., Tsang, M., Friedmann, M., Weatherbee, J. A., Zhou, L., Yamauchi, A., Bloom, E. T., Mietz, J., John, S. & Leonard, W. J. (1995) *Immunity* 2, 331–339.
38. Matthews, D. J., Clark, P. A., Herbert, J., Morgan, G., Armitage, R. J., Kinnon, C., Minty, A., Grabstein, K. H., Caput, D., Ferrara, P. & Callard, R. (1995) *Blood* 85, 38–42.
39. Izuhara, K., Heike, T., Otsuka, T., Yamaoka, K., Mayumi, M., Imamura, T., Niho, Y. & Harada, N. (1996) *J. Biol. Chem.* 271, 619–622.
40. Callard, R. E., Matthews, D. & Hibbert, L. (1996) *Immunol. Today* 17, 108–110.
41. Hilton, D. J., Zhang, J.-G., Metcalf, D., Alexander, W. S., Nicola, N. A & Willson, T. A., (1996) *Proc. Natl. Acad. Sci. USA.* 93, 497–501.
42. Caput, D., Laurent, P., Kaghad, M., Lelias, J.-M., Lefort, S., Vita, N & Ferrara, P. (1996) *J. Biol. Chem.* 271, 16921–16926.
43. Bazan, J. F. *Proc. Natl. Acad. Sci. USA.* 87, 6934–6938.
44. Gauchat, J.-F., Henchoz, S., Fattah, D., Mazzei, G., Aubry, J.-P., Jomotte, T., Dash, L., Page, K. Solari, R. Aldebert, D., Capron. M., Dahinden, C. & Bonnefoy, J.-Y. (1995) *Eur. J. Immunol.* 25, 863–865.
45. Pochon, S., Graber, P., Yeager, M., Jansen, K., Bernard, A. R., Aubry, J.-P. & Bonnefoy, J.-Y. (1992) *J. Exp. Med.* 176, 389–397.

46. Life, P., Gauchat, J.-F., Schnuriger, V., Estoppey, S., Mazzei, G., Durandy, A., Fisher, A. & Bonnefoy, J.-Y. (1994) *J. Exp. Med.* 180, 1775–1784.
47. Macchi, P., Villa, A., Giliani, S., Sacco, M. G., Frattini, A., Porta, F., Ugazio, A. G., Johnston, J. A., Candotti, F., O'Shea, J. J., Vezzoni, P. & Notarangelo, L. D. (1995) *Nature* (London) 377, 65–68.
48. Okayama, H., Kawaichi, M., Brownstein, M., Lee, F., Yokota, T. & Arai, K. (1987) *Methods Enzymol.* 154, 3–28.
49. Feinberg, A. P. & Vogeltein, B. (1983) *Anal. Biochem.* 132, 6-
50. Takabe, Y., Seiki, M., Fujisawa, J., Hoy, P., Yokota, K., Arai, K., Yoshida, M. & Arai, N. (1988) *Mol. Cell. Biol.* 8, 466–472.
51. Galizzi, J. P., Zuber, C. E., Harada, N., Gorman, D. M., Djossou, O., Kastelein, R., Banchereau, J., Howard, M. & Miyajima, A. (1990) *Int. Immunol.* 2, 669–675.
52. Takeshita, T., Asao, H., Ohtani, K., Ishii, N., Kumaki, S., Tanaka, N., Munakata, H., Nakamura, M. & Sugamura, K. (1992) *Science* 257, 379–382.
53. Melton, D. A., Krieg, P. A., Rebagliati, M. R., Maniatis, T., Zinn, K. & Green, M. R. (1997) *Nucleic Acids Res.* 12, 7035-
54. Gauchat, J.-F., Lebman, D. A., Coffman, R. L. & de Vries, J. E. (1990) *J. Exp. Med.* 172, 463–473.
55. Gauchat, J.-F. Gauchat, D., de Weck, A. L. & Stadler, B. M. (1989) *Eur. J. Immunol.* 19, 1079-
56. Stahl, N., Farrugella, T. J., Boulton, T. G., Zhong, Z., Darnell, J. E. Jr. & Yancopoulos, G. D. *Science* 267, 1349–1353.
57. Gauchat, J.-F., Gascan, H., de Waal Malefyt, R. & de Vries, J. E. (1992) *J. Immunol.* 148, 2291–2299.
58. Moser, R., Fehr, J. and Bruijnzeel, P.L. *J. Immunol.* 1992 149: 1432.
59. Moser, R., Groscurth, P., Carballido, J.M., Bruijnzeel, P.L., Blaser, K., Heusser, C.H. and Fehr, J. *J. Lab Clinical Med.* 1993 122: 567

We claim:

1. An isolated polypeptide which is capable of binding human IL-13 and/or of binding human IL-4 in the presence of IL-4 R α or which is bound to human IL-13 and/or human IL-4; which:
   comprises the amino acid sequence shown in SEQ ID NO:9.

2. A polypeptide according to claim 1 which consists of the complete amino acid sequence represented by amino acids 1 to 427, shown in SEQ ID No:9.

3. An isolated polypeptide which comprises the extracellular sequence represented by amino acids 27 to 427, shown in SEQ ID NO:9.

4. An isolated polypeptide which has a sequence that differs from that shown in SEQ ID NO:9 wherein the T residue number 130 and G residue number 358 shown in SEQ ID NO:9 are replaced by I and D residues, respectively.

5. A composition comprising the polypeptide according to claim 1 and a membrane, wherein said polypeptide is bound to said membrane.

6. A polypeptide according to claim 1 which is in soluble form.

7. A polypeptide according to claim 3 which consists of the amino acids 27 to 347 shown in SEQ ID NO:9.

8. A composition comprising the isolated polypeptide according to claim 1 in admixture with a carrier.

* * * * *

UNITED STATES PATENT AND TRADEMARK OFFICE
CERTIFICATE OF CORRECTION

PATENT NO.     : 6,143,871
DATED          : November 7, 2000
INVENTOR(S)    : Bonnefoy et al.

It is certified that error appears in the above-identified patent and that said Letters Patent is hereby corrected as shown below:

Drawings,
Figure 5, panel A, change "IL-4R" to -- IL-4Rα --.
Figure 5, panel C, change "IL-4R/IL-13Rα1" to -- IL-4Rα/IL-13Rα1 --.

Column 12,
Lines 13-17 delete "Receptor binding analysis of radiolabeled IL4 (▲) and 1L13 (●) was performed with COS7 cells transiently transfected with (A) the cDNA of either the human IL4Rα (full line), the IL13Ra1 (dashed line) or (B) contransfected with both cDNAs." and replace with -- Receptor binding analysis of radiolabeled IL4 (▲) and IL13 (●) was performed with COS7 cells transiently transfected with cDNA of either the human IL4Rα (panel A), the IL13α1 (panel B) or cotransfected with both cDNAs (panel C). --

Column 15,
Line 41, table 1, change "$R_{max}$" to -- $B_{max}$ --.

Signed and Sealed this

Sixteenth Day of September, 2003

JAMES E. ROGAN
*Director of the United States Patent and Trademark Office*

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (v) FRAGMENT TYPE: linear (xi) SEQUENCE DESCRIPTION: SEQ ID NO:1:

Tyr Xaa Xaa Gln
1

(2) INFORMATION FOR SEQ ID NO:2:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (v) FRAGMENT TYPE: linear (xi) SEQUENCE DESCRIPTION: SEQ ID NO:2:

Trp Ser Xaa Trp Ser
1               5

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear

```
        (ii) MOLECULE TYPE: DNA (genomic)

(v) FRAGMENT TYPE: linear (xi) SEQUENCE DESCRIPTION: SEQ ID NO:3:

CTGAGCTACA TGAAGTGTTC TTGGCTCCCT                                       30

(2) INFORMATION FOR SEQ ID NO:4:

(i) SEQUENCE CHARACTERISTICS:
             (A) LENGTH: 30 base pairs
             (B) TYPE: nucleic acid
             (C) STRANDEDNESS: single
             (D) TOPOLOGY: linear (ii) MOLECULE TYPE: DNA (genomic)

(v) FRAGMENT TYPE: linear (xi) SEQUENCE DESCRIPTION: SEQ ID NO:4:

CAGAGTTTGT CATCCTCATA GCATAACTTA                                       30

(2) INFORMATION FOR SEQ ID NO:5:

(i) SEQUENCE CHARACTERISTICS:
             (A) LENGTH: 30 base pairs
             (B) TYPE: nucleic acid
             (C) STRANDEDNESS: single
             (D) TOPOLOGY: linear (ii) MOLECULE TYPE: DNA (genomic)

(v) FRAGMENT TYPE: linear (xi) SEQUENCE DESCRIPTION: SEQ ID NO:5:

AATACCACTC CCGACACTAA CTATACTCTC                                       30

(2) INFORMATION FOR SEQ ID NO:6:

(i) SEQUENCE CHARACTERISTICS:
             (A) LENGTH: 30 base pairs
             (B) TYPE: nucleic acid
             (C) STRANDEDNESS: single
             (D) TOPOLOGY: linear (ii) MOLECULE TYPE: DNA (genomic)

(v) FRAGMENT TYPE: linear (xi) SEQUENCE DESCRIPTION: SEQ ID NO:6:

GGAGAAATGG CTTTCGTTTG CTTGGCTATC                                       30

(2) INFORMATION FOR SEQ ID NO:7:

(i) SEQUENCE CHARACTERISTICS:
             (A) LENGTH: 30 base pairs
             (B) TYPE: nucleic acid
             (C) STRANDEDNESS: single
             (D) TOPOLOGY: linear (ii) MOLECULE TYPE: DNA (genomic)

(v) FRAGMENT TYPE: linear (xi) SEQUENCE DESCRIPTION: SEQ ID NO:7:

TACCATGTCT CTTGATATGG AAAGTCTTCA                                       30

(2) INFORMATION FOR SEQ ID NO:8:
```

(i) SEQUENCE CHARACTERISTICS:
     (A) LENGTH: 4038 base pairs
     (B) TYPE: nucleic acid
     (C) STRANDEDNESS: single
     (D) TOPOLOGY: linear (ii) MOLECULE TYPE: DNA (genomic)

(v) FRAGMENT TYPE: linear (ix) FEATURE:
     (A) NAME/KEY: CDS
     (B) LOCATION: 43..1323

(xi) SEQUENCE DESCRIPTION: SEQ ID NO:8:

```
GCCAAGGCTC CAGCCCGGCC GGGCTCCGAG GCGAGAGGCT GC ATG GAG TGG CCG                54
                                                Met Glu Trp Pro
                                                  1

GCG CGG CTC TGC GGG CTG TGG GCG CTG CTG CTC TGC GCC GGC GGC GGG              102
Ala Arg Leu Cys Gly Leu Trp Ala Leu Leu Leu Cys Ala Gly Gly Gly
  5                  10                  15                  20

GGC GGG GGC GGG GGC GCC GCG CCT ACG GAA ACT CAG CCA CCT GTG ACA              150
Gly Gly Gly Gly Gly Ala Ala Pro Thr Glu Thr Gln Pro Pro Val Thr
                 25                  30                  35

AAT TTG AGT GTC TCT GTT GAA AAC CTC TGC ACA GTA ATA TGG ACA TGG              198
Asn Leu Ser Val Ser Val Glu Asn Leu Cys Thr Val Ile Trp Thr Trp
         40                  45                  50

AAT CCA CCC GAG GGA GCC AGC TCA AAT TGT AGT CTA TGG TAT TTT AGT              246
Asn Pro Pro Glu Gly Ala Ser Ser Asn Cys Ser Leu Trp Tyr Phe Ser
     55                  60                  65

CAT TTT GGC GAC AAA CAA GAT AAG AAA ATA GCT CCG GAA ACT CGT CGT              294
His Phe Gly Asp Lys Gln Asp Lys Lys Ile Ala Pro Glu Thr Arg Arg
 70                  75                  80

TCA ATA GAA GTA CCC CTG AAT GAG AGG ATT TGT CTG CAA GTG GGG TCC              342
Ser Ile Glu Val Pro Leu Asn Glu Arg Ile Cys Leu Gln Val Gly Ser
 85                  90                  95                 100

CAG TGT AGC ACC AAT GAG AGT GAG AAG CCT AGC ATT TTG GTT GAA AAA              390
Gln Cys Ser Thr Asn Glu Ser Glu Lys Pro Ser Ile Leu Val Glu Lys
                105                 110                 115

TGC ATC TCA CCC CCA GAA GGT GAT CCT GAG TCT GCT GTG ACT GAG CTT              438
Cys Ile Ser Pro Pro Glu Gly Asp Pro Glu Ser Ala Val Thr Glu Leu
            120                 125                 130

CAA TGC ATT TGG CAC AAC CTG AGC TAC ATG AAG TGT TCT TGG CTC CCT              486
Gln Cys Ile Trp His Asn Leu Ser Tyr Met Lys Cys Ser Trp Leu Pro
        135                 140                 145

GGA AGG AAT ACC AGT CCC GAC ACT AAC TAT ACT CTC TAC TAT TGG CAC              534
Gly Arg Asn Thr Ser Pro Asp Thr Asn Tyr Thr Leu Tyr Tyr Trp His
    150                 155                 160

AGA AGC CTG GAA AAA ATT CAT CAA TGT GAA AAC ATC TTT AGA GAA GGC              582
Arg Ser Leu Glu Lys Ile His Gln Cys Glu Asn Ile Phe Arg Glu Gly
165                 170                 175                 180

CAA TAC TTT GGT TGT TCC TTT GAT CTG ACC AAA GTG AAG GAT TCC AGT              630
Gln Tyr Phe Gly Cys Ser Phe Asp Leu Thr Lys Val Lys Asp Ser Ser
                185                 190                 195

TTT GAA CAA CAC AGT GTC CAA ATA ATG GTC AAG GAT AAT GCA GGA AAA              678
Phe Glu Gln His Ser Val Gln Ile Met Val Lys Asp Asn Ala Gly Lys
            200                 205                 210

ATT AAA CCA TCC TTC AAT ATA GTG CCT TTA ACT TCC CGT GTG AAA CCT              726
Ile Lys Pro Ser Phe Asn Ile Val Pro Leu Thr Ser Arg Val Lys Pro
        215                 220                 225

GAT CCT CCA CAT ATT AAA AAC CTC TCC TTC CAC AAT GAT GAC CTA TAT              774
Asp Pro Pro His Ile Lys Asn Leu Ser Phe His Asn Asp Asp Leu Tyr
    230                 235                 240
```

```
GTG CAA TGG GAG AAT CCA CAG AAT TTT ATT AGC AGA TGC CTA TTT TAT      822
Val Gln Trp Glu Asn Pro Gln Asn Phe Ile Ser Arg Cys Leu Phe Tyr
245                 250                 255                 260

GAA GTA GAA GTC AAT AAC AGC CAA ACT GAG ACA CAT AAT GTT TTC TAC      870
Glu Val Glu Val Asn Asn Ser Gln Thr Glu Thr His Asn Val Phe Tyr
                265                 270                 275

GTC CAA GAG GCT AAA TGT GAG AAT CCA GAA TTT GAG AGA AAT GTG GAG      918
Val Gln Glu Ala Lys Cys Glu Asn Pro Glu Phe Glu Arg Asn Val Glu
            280                 285                 290

AAT ACA TCT TGT TTC ATG GTC CCT GGT GTT CTT CCT GAT ACT TTG AAC      966
Asn Thr Ser Cys Phe Met Val Pro Gly Val Leu Pro Asp Thr Leu Asn
        295                 300                 305

ACA GTC AGA ATA AGA GTC AAA ACA AAT AAG TTA TGC TAT GAG GAT GAC     1014
Thr Val Arg Ile Arg Val Lys Thr Asn Lys Leu Cys Tyr Glu Asp Asp
    310                 315                 320

AAA CTC TGG AGT AAT TGG AGC CAA GAA ATG AGT ATA GGT AAG AAG CGC     1062
Lys Leu Trp Ser Asn Trp Ser Gln Glu Met Ser Ile Gly Lys Lys Arg
325                 330                 335                 340

AAT TCC ACA CTC TAC ATA ACC ATG TTA CTC ATT GTT CCA GTC ATC GTC     1110
Asn Ser Thr Leu Tyr Ile Thr Met Leu Leu Ile Val Pro Val Ile Val
                345                 350                 355

GCA GGT GCA ATC ATA GTA CTC CTG CTT TAC CTA AAA AGG CTC AAG ATT     1158
Ala Gly Ala Ile Ile Val Leu Leu Leu Tyr Leu Lys Arg Leu Lys Ile
            360                 365                 370

ATT ATA TTC CCT CCA ATT CCT GAT CCT GGC AAG ATT TTT AAA GAA ATG     1206
Ile Ile Phe Pro Pro Ile Pro Asp Pro Gly Lys Ile Phe Lys Glu Met
        375                 380                 385

TTT GGA GAC CAG AAT GAT GAT ACT CTG CAC TGG AAG AAG TAC GAC ATC     1254
Phe Gly Asp Gln Asn Asp Asp Thr Leu His Trp Lys Lys Tyr Asp Ile
    390                 395                 400

TAT GAG AAG CAA ACC AAG GAG GAA ACC GAC TCT GTA GTG CTG ATA GAA     1302
Tyr Glu Lys Gln Thr Lys Glu Glu Thr Asp Ser Val Val Leu Ile Glu
405                 410                 415                 420

AAC CTG AAG AAA GCC TCT CAG TGATGGAGAT AATTTATTTT TACCTTCACT        1353
Asn Leu Lys Lys Ala Ser Gln
                425

GTGACCTTGA GAAGATTCTT CCCATTCTCC ATTTGTTATC TGGGAACTTA TTAAATGGAA   1413

ACTGAAACTA CTGCACCATT TAAAAACAGG CAGCTCATAA GAGCCACAGG TCTTTATGTT   1473

GAGTCGCGCA CCGAAAAACT AAAAATAATG GGCGCTTTGG AGAAGAGTGT GGAGTCATTC   1533

TCATTGAATT ATAAAAGCCA GCAGGCTTCA AACTAGGGGA CAAAGCAAAA AGTGATGATA   1593

GTGGTGGAGT TAATCTTATC AAGAGTTGTG ACAACTTCCT GAGGGATCTA TACTTGCTTT   1653

GTGTTCTTTG TGTCAACATG AACAAATTTT ATTTGTAGGG GAACTCATTT GGGGTGCAAA   1713

TGCTAATGTC AAACTTGAGT CACAAAGAAC ATGTAGAAAA CAAAATGGAT AAAATCTGAT   1773

ATGTATTGTT TGGGATCCTA TTGAACCATG TTTGTGGCTA TTAAAACTCT TTTAACAGTC   1833

TGGGCTGGGT CCGGTGGCTC ACGCCTGTAA TCCCAGCAAT TGGGAGTCC GAGGCGGGCG    1893

GATCACTCGA GGTCAGGAGT TCCAGACCAG CCTGACCAAA ATGGTGAAAC CTCCTCTCTA   1953

CTAAAACTAC AAAAATTAAC TGGGTGTGGT GGCGCGTGCC TGTAATCCCA GCTACTCGGG   2013

AAGCTGAGGC AGGTGAATTG TTTGAACCTG GGAGGTGGAG GTTGCAGTGA GCAGAGATCA   2073

CACCACTGCA CTCTAGCCTG GGTGACAGAG CAAGACTCTG TCTAAAAAAC AAAACAAAAC   2133

AAAACAAAAC AAAAAAACCT CTTAATATTC TGGAGTCATC ATTCCCTTCG ACAGCATTTT   2193

CCTCTGCTTT GAAAGCCCCA GAAATCAGTG TTGGCCATGA TGACAACTAC AGAAAAACCA   2253
```

```
GAGGCAGCTT CTTTGCCAAG ACCTTTCAAA GCCATTTTAG GCTGTTAGGG GCAGTGGAGG    2313

TAGAATGACT CCTTGGGTAT TAGAGTTTCA ACCATGAAGT CTCTAACAAT GTATTTCTT    2373

CACCTCTGCT ACTCAAGTAG CATTTACTGT GTCTTTGGTT TGTGCTAGGC CCCCGGGTGT    2433

GAAGCACAGA CCCCTTCCAG GGGTTTACAG TCTATTTGAG ACTCCTCAGT TCTTGCCACT    2493

TTTTTTTTTA ATCTCCACCA GTCATTTTTC AGACCTTTTA ACTCCTCAAT TCCAACACTG    2553

ATTTCCCCTT TTGCATTCTC CCTCCTTCCC TTCCTTGTAG CCTTTTGACT TTCATTGGAA    2613

ATTAGGATGT AAATCTGCTC AGGAGACCTG GAGGAGCAGA GGATAATTAG CATCTCAGGT    2673

TAAGTGTGAG TAATCTGAGA AACAATGACT AATTCTTGCA TATTTTGTAA CTTCCATGTG    2733

AGGGTTTTCA GCATTGATAT TTGTGCATTT TCTAAACAGA GATGAGGTGG TATCTTCACG    2793

TAGAACATTG GTATTCGCTT GAGAAAAAAA GAATAGTTGA ACCTATTTCT CTTTCTTTAC    2853

AAGATGGGTC CAGGATTCCT CTTTTCTCTG CCATAAATGA TTAATTAAAT AGCTTTTGTG    2913

TCTTACATTG GTAGCCAGCC AGCCAAGGCT CTGTTTATGC TTTTGGGGGG CATATATTGG    2973

GTTCCATTCT CACCTATCCA CACAACATAT CCGTATATAT CCCCTCTACT CTTACTTCCC    3033

CCAAATTTAA AGAAGTATGG GAAATGAGAG GCATTTCCCC CACCCCATTT CTCTCCTCAC    3093

ACACAGACTC ATATTACTGG TAGGAACTTG AGAACTTTAT TTCCAAGTTG TTCAAACATT    3153

TACCAATCAT ATTAATACAA TGATGCTATT TGCAATTCCT GCTCCTAGGG GAGGGGAGAT    3213

AAGAAACCCT CACTCTCTAC AGGTTTGGGT ACAAGTGGCA ACCTGCTTCC ATGGCCGTGT    3273

AGAAGCATGG TGCCCTGGCT TCTCTGAGGA AGCTGGGGTT CATGACAATG GCAGATGTAA    3333

AGTTATTCTT GAAGTCAGAT TGAGGCTGGG AGACAGCCGT AGTAGATGTT CTACTTTGTT    3393

CTGCTGTTCT CTAGAAAGAA TATTTGGTTT TCCTGTATAG GAATGAGATT AATTCCTTTC    3453

CAGGTATTTT ATAATTCTGG GAAGCAAAAC CCATGCCTCC CCCTAGCCAT TTTTACTGTT    3513

ATCCTATTTA GATGGCCATG AAGAGGATGC TGTGAAATTC CCAACAAACA TTGATGCTGA    3573

CAGTCATGCA GTCTGGGAGT GGGGAAGTGA TCTTTTGTTC CCATCCTCTT CTTTTAGCAG    3633

TAAAATAGCT GAGGGAAAAG GGAGGGAAAA GGAAGTTATG GAATACCTG TGGTGGTTGT    3693

GATCCCTAGG TCTTGGGAGC TCTTGGAGGT GTCTGTATCA GTGGATTTCC CATCCCCTGT    3753

GGGAAATTAG TAGGCTCATT TACTGTTTTA GGTCTAGCCT ATGTGGATTT TTTCCTAACA    3813

TACCTAAGCA AACCCAGTGT CAGGATGGTA ATTCTTATTC TTTCGTTCAG TTAAGTTTTT    3873

CCCTTCATCT GGGCACTGAA GGGATATGTG AAACAATGTT AACATTTTTG GTAGTCTTCA    3933

ACCAGGGATT GTTTCTGTTT AACTTCTTAT AGGAAAGCTT GAGTAAAATA AATATTGTCT    3993

TTTTGTATGT CAAGCGGGCC GCCACCGCGG TGGAAACTCC AGCTT                   4038
```

(2) INFORMATION FOR SEQ ID NO:9:

(i) SEQUENCE CHARACTERISTICS:
        (A) LENGTH: 427 amino acids
        (B) TYPE: amino acid
        (D) TOPOLOGY: linear (ii) MOLECULE TYPE: protein (xi) SEQUENCE DESCRIPTION: SEQ ID NO:9:

```
Met Glu Trp Pro Ala Arg Leu Cys Gly Leu Trp Ala Leu Leu Leu Cys
  1               5                  10                  15

Ala Gly Gly Gly Gly Gly Gly Gly Ala Ala Pro Thr Glu Thr Gln
                 20                  25                  30

Pro Pro Val Thr Asn Leu Ser Val Ser Val Glu Asn Leu Cys Thr Val
```

```
             35                  40                  45
Ile Trp Thr Trp Asn Pro Pro Glu Gly Ala Ser Ser Asn Cys Ser Leu
    50                  55                  60

Trp Tyr Phe Ser His Phe Gly Asp Lys Gln Asp Lys Lys Ile Ala Pro
65                  70                  75                  80

Glu Thr Arg Arg Ser Ile Glu Val Pro Leu Asn Glu Arg Ile Cys Leu
                85                  90                  95

Gln Val Gly Ser Gln Cys Ser Thr Asn Glu Ser Glu Lys Pro Ser Ile
            100                 105                 110

Leu Val Glu Lys Cys Ile Ser Pro Pro Glu Gly Asp Pro Glu Ser Ala
        115                 120                 125

Val Thr Glu Leu Gln Cys Ile Trp His Asn Leu Ser Tyr Met Lys Cys
    130                 135                 140

Ser Trp Leu Pro Gly Arg Asn Thr Ser Pro Asp Thr Asn Tyr Thr Leu
145                 150                 155                 160

Tyr Tyr Trp His Arg Ser Leu Glu Lys Ile His Gln Cys Glu Asn Ile
                165                 170                 175

Phe Arg Glu Gly Gln Tyr Phe Gly Cys Ser Phe Asp Leu Thr Lys Val
            180                 185                 190

Lys Asp Ser Ser Phe Glu Gln His Ser Val Gln Ile Met Val Lys Asp
        195                 200                 205

Asn Ala Gly Lys Ile Lys Pro Ser Phe Asn Ile Val Pro Leu Thr Ser
    210                 215                 220

Arg Val Lys Pro Asp Pro Pro His Ile Lys Asn Leu Ser Phe His Asn
225                 230                 235                 240

Asp Asp Leu Tyr Val Gln Trp Glu Asn Pro Gln Asn Phe Ile Ser Arg
                245                 250                 255

Cys Leu Phe Tyr Glu Val Glu Val Asn Asn Ser Gln Thr Glu Thr His
            260                 265                 270

Asn Val Phe Tyr Val Gln Glu Ala Lys Cys Glu Asn Pro Glu Phe Glu
        275                 280                 285

Arg Asn Val Glu Asn Thr Ser Cys Phe Met Val Pro Gly Val Leu Pro
    290                 295                 300

Asp Thr Leu Asn Thr Val Arg Ile Arg Val Lys Thr Asn Lys Leu Cys
305                 310                 315                 320

Tyr Glu Asp Asp Lys Leu Trp Ser Asn Trp Ser Gln Glu Met Ser Ile
                325                 330                 335

Gly Lys Lys Arg Asn Ser Thr Leu Tyr Ile Thr Met Leu Leu Ile Val
            340                 345                 350

Pro Val Ile Val Ala Gly Ala Ile Ile Val Leu Leu Leu Tyr Leu Lys
        355                 360                 365

Arg Leu Lys Ile Ile Ile Phe Pro Pro Ile Pro Asp Pro Gly Lys Ile
    370                 375                 380

Phe Lys Glu Met Phe Gly Asp Gln Asn Asp Asp Thr Leu His Trp Lys
385                 390                 395                 400

Lys Tyr Asp Ile Tyr Glu Lys Gln Thr Lys Glu Glu Thr Asp Ser Val
                405                 410                 415

Val Leu Ile Glu Asn Leu Lys Lys Ala Ser Gln
            420                 425
```